(12) United States Patent
Genstler et al.

(10) Patent No.: US 11,458,290 B2
(45) Date of Patent: Oct. 4, 2022

(54) ULTRASOUND SYSTEM

(75) Inventors: Curtis Genstler, Snohomish, WA (US);
Douglas R. Hansmann, Bainbridge Island, WA (US)

(73) Assignee: EKOS CORPORATION, Bothell, WA (US)

( * ) Notice: Subject to any disclaimer, the term of this patent is extended or adjusted under 35 U.S.C. 154(b) by 1179 days.

(21) Appl. No.: 13/468,920

(22) Filed: May 10, 2012

(65) Prior Publication Data
US 2012/0289889 A1 Nov. 15, 2012

Related U.S. Application Data

(60) Provisional application No. 61/579,545, filed on Dec. 22, 2011, provisional application No. 61/485,022, filed on May 11, 2011.

(51) Int. Cl.
*A61M 37/00* (2006.01)
*A61B 17/22* (2006.01)
*A61B 17/00* (2006.01)

(52) U.S. Cl.
CPC ..... *A61M 37/0092* (2013.01); *A61B 17/2202* (2013.01); *A61B 2017/00088* (2013.01);
(Continued)

(58) Field of Classification Search
CPC ...... A61B 17/2202; A61B 2017/00088; A61B 2017/00092; A61B 2017/00101;
(Continued)

(56) References Cited

U.S. PATENT DOCUMENTS

| 3,352,303 A | 11/1967 | Delaney |
| 3,430,625 A | 3/1969 | McLeod, Jr. |

(Continued)

FOREIGN PATENT DOCUMENTS

| DE | 40 05 743 | 8/1991 |
| EP | 0 529 675 | 3/1993 |

(Continued)

OTHER PUBLICATIONS

Chamsuddin et al., "Catheter-directed Thrombolysis with the Endowave System in the Treatment of Acute Massive Pulmonary Embolism: A Retrospective Multicenter Case Series," Journal of Vascular and Interventional Radiology, Mar. 2008, vol. 19, No. 3, pp. 372-376.
(Continued)

*Primary Examiner* — Jason E Flick
(74) *Attorney, Agent, or Firm* — Seager, Tufte & Wickhem, LLP

(57) ABSTRACT

A catheter system for delivering ultrasonic energy to a treatment site within a body lumen, the catheter comprises a tubular body having a proximal end, a distal end and an energy delivery section positioned between the proximal end and the distal end and a plurality of ultrasound radiating members in the energy delivery section. The plurality of ultrasound radiating members are allocated into electrical groups comprising more than one ultrasound radiating member. Members of one electrical group are spatially interdigitated with members of another electrical group.

8 Claims, 19 Drawing Sheets

(52) U.S. Cl.
CPC .............. *A61B 2017/00092* (2013.01); *A61B 2017/00101* (2013.01); *A61B 2017/22021* (2013.01); *A61B 2017/22084* (2013.01); *A61B 2017/22088* (2013.01)

(58) Field of Classification Search
CPC ........... A61B 2017/22021; A61B 2017/22084; A61B 2017/22088; A61B 17/22012; A61B 8/445; A61B 17/22; A61B 17/22004; A61B 2017/22028; A61B 2017/22051; A61B 2019/5276; A61B 17/12022; A61B 17/320068; A61M 37/0092; A61M 2205/058; A61N 2007/0078; A61N 7/00
USPC ........................................................ 604/22
See application file for complete search history.

(56) References Cited

U.S. PATENT DOCUMENTS

| | | | |
|---|---|---|---|
| 3,433,226 A | 3/1969 | Boyd | |
| 3,565,062 A | 2/1971 | Kuris | |
| 3,827,115 A | 8/1974 | Bom | |
| 3,861,391 A | 1/1975 | Antonevich et al. | |
| 3,941,122 A | 3/1976 | Jones | |
| 3,976,987 A | 8/1976 | Anger | |
| 4,040,414 A | 8/1977 | Suroff | |
| 4,192,294 A | 3/1980 | Vasilevsky et al. | |
| 4,309,989 A | 1/1982 | Fahim | |
| 4,319,580 A | 3/1982 | Colley et al. | |
| 4,354,502 A | 10/1982 | Colley et al. | |
| 4,531,943 A | 7/1985 | Van Tassel | |
| 4,549,533 A | 10/1985 | Cain et al. | |
| 4,587,975 A | 5/1986 | Salo et al. | |
| 4,682,596 A | 7/1987 | Bales et al. | |
| 4,692,139 A | 9/1987 | Stiles | |
| 4,709,698 A | 12/1987 | Johnston et al. | |
| 4,750,902 A | 6/1988 | Wuchinich | |
| 4,754,752 A | 7/1988 | Ginsburg et al. | |
| 4,770,185 A | 9/1988 | Silverstein et al. | |
| 4,808,153 A | 2/1989 | Parisi | |
| 4,821,740 A | 4/1989 | Tachibana et al. | |
| 4,841,977 A | 6/1989 | Griffith et al. | |
| 4,870,953 A | 10/1989 | DonMicheal et al. | |
| 4,920,954 A | 5/1990 | Alliger | |
| 4,921,478 A | 5/1990 | Solano et al. | |
| 4,924,863 A | 5/1990 | Sterzer | |
| 4,933,843 A | 6/1990 | Scheller et al. | |
| 4,936,281 A | 6/1990 | Stasz | |
| 4,948,587 A | 8/1990 | Kost et al. | |
| 4,951,677 A | 8/1990 | Crowley | |
| 4,953,565 A | 9/1990 | Tachibana et al. | |
| 4,960,109 A | 10/1990 | Lele | |
| 4,971,991 A | 11/1990 | Umemura et al. | |
| 5,007,438 A | 4/1991 | Tachibana et al. | |
| 5,021,044 A | 6/1991 | Sharkawy | |
| 5,026,387 A | 6/1991 | Thomas | |
| 5,053,008 A * | 10/1991 | Bajaj | 604/104 |
| 5,058,570 A | 10/1991 | Idemoto et al. | |
| 5,059,851 A | 10/1991 | Corl | |
| 5,069,664 A | 12/1991 | Guess | |
| 5,076,276 A | 12/1991 | Sakurai et al. | |
| 5,088,499 A | 2/1992 | Unger | |
| 5,108,369 A | 4/1992 | Ganguly et al. | |
| 5,129,883 A | 7/1992 | Black | |
| 5,149,319 A | 9/1992 | Unger | |
| 5,158,071 A | 10/1992 | Umemura et al. | |
| 5,163,421 A | 11/1992 | Bernstein et al. | |
| 5,163,436 A | 11/1992 | Saitoh et al. | |
| 5,178,620 A | 1/1993 | Eggers et al. | |
| 5,185,071 A | 2/1993 | Serwer et al. | |
| 5,197,946 A | 3/1993 | Tachibana | |
| 5,226,421 A | 7/1993 | Frisbie | |
| 5,250,034 A | 10/1993 | Appling | |
| 5,261,291 A | 11/1993 | Schoch et al. | |
| 5,267,954 A | 12/1993 | Nita | |
| 5,267,985 A | 12/1993 | Shimada | |
| 5,269,291 A | 12/1993 | Carter | |
| 5,271,406 A | 12/1993 | Ganguly | |
| 5,279,546 A | 1/1994 | Mische et al. | |
| 5,282,785 A | 2/1994 | Shapland et al. | |
| 5,286,254 A | 2/1994 | Shapland | |
| 5,295,484 A | 3/1994 | Marcus et al. | |
| 5,304,115 A | 4/1994 | Pflueger | |
| 5,307,816 A | 5/1994 | Hashimoto | |
| 5,312,328 A | 5/1994 | Nita et al. | |
| 5,313,949 A | 5/1994 | Yock | |
| 5,315,998 A | 5/1994 | Tachibana et al. | |
| 5,318,014 A | 6/1994 | Carter | |
| 5,323,769 A | 6/1994 | Bommannan | |
| 5,326,342 A | 7/1994 | Pflueger | |
| 5,327,891 A | 7/1994 | Rammler | |
| 5,328,470 A | 7/1994 | Nabel | |
| 5,342,292 A | 8/1994 | Nita et al. | |
| 5,344,395 A | 9/1994 | Whalen et al. | |
| 5,344,435 A | 9/1994 | Turner | |
| 5,345,940 A | 9/1994 | Seward | |
| 5,348,481 A | 9/1994 | Oritz | |
| 5,351,693 A | 10/1994 | Taimisto | |
| 5,353,798 A | 10/1994 | Sieben | |
| 5,354,279 A | 10/1994 | Hofling | |
| 5,362,309 A | 11/1994 | Carter | |
| 5,363,853 A | 11/1994 | Lieber | |
| 5,368,036 A | 11/1994 | Tanaka et al. | |
| 5,368,557 A | 11/1994 | Nita | |
| 5,368,558 A | 11/1994 | Nita | |
| 5,370,675 A | 12/1994 | Edwards | |
| 5,372,138 A | 12/1994 | Crowley et al. | |
| 5,380,273 A | 1/1995 | Dubrul et al. | |
| 5,385,148 A | 1/1995 | Lesh et al. | |
| 5,390,678 A | 2/1995 | Gesswein | |
| 5,397,293 A | 3/1995 | Alliger | |
| 5,399,158 A * | 3/1995 | Lauer et al. | 604/22 |
| 5,401,237 A | 3/1995 | Tachibana et al. | |
| 5,405,322 A | 4/1995 | Lennox et al. | |
| 5,421,338 A | 6/1995 | Crowley | |
| 5,423,797 A | 6/1995 | Adrian et al. | |
| 5,431,663 A | 7/1995 | Carter | |
| 5,440,914 A | 8/1995 | Tachibana et al. | |
| 5,445,155 A | 8/1995 | Sieben | |
| 5,447,509 A | 9/1995 | Mills et al. | |
| 5,447,510 A | 9/1995 | Jensen | |
| 5,453,575 A | 9/1995 | O'Donell et al. | |
| 5,456,259 A | 10/1995 | Barlow et al. | |
| 5,458,568 A | 10/1995 | Racchini | |
| 5,462,523 A | 10/1995 | Samson | |
| 5,465,726 A | 11/1995 | Dickinson | |
| 5,474,530 A | 12/1995 | Passafaro | |
| 5,474,531 A | 12/1995 | Carter | |
| 5,498,236 A | 3/1996 | Dubrul et al. | |
| 5,498,238 A | 3/1996 | Shapland | |
| 5,509,896 A | 4/1996 | Carter | |
| 5,514,092 A | 5/1996 | Forman | |
| 5,520,189 A | 5/1996 | Malinowski | |
| 5,523,058 A | 6/1996 | Umemura | |
| 5,533,986 A | 7/1996 | Mottola | |
| 5,542,917 A | 8/1996 | Nita et al. | |
| 5,542,935 A | 8/1996 | Unger et al. | |
| 5,558,092 A | 9/1996 | Unger et al. | |
| 5,560,362 A | 10/1996 | Sliwa, Jr. et al. | |
| 5,569,197 A | 10/1996 | Helmus | |
| 5,582,586 A | 12/1996 | Tachibana et al. | |
| 5,588,432 A | 12/1996 | Crowley | |
| 5,603,327 A | 2/1997 | Eberle | |
| 5,603,694 A | 2/1997 | Brown | |
| 5,606,974 A | 3/1997 | Castellano | |
| 5,617,851 A | 4/1997 | Lipkovker | |
| 5,618,275 A | 4/1997 | Bock | |
| 5,620,409 A | 4/1997 | Gans et al. | |
| 5,620,479 A | 4/1997 | Diederich | |
| 5,624,382 A | 4/1997 | Oppelt | |
| 5,628,728 A | 5/1997 | Tachibana et al. | |
| 5,628,730 A | 5/1997 | Shapland | |
| 5,630,837 A | 5/1997 | Crowley | |

(56) References Cited

U.S. PATENT DOCUMENTS

| | | |
|---|---|---|
| 5,648,098 A | 7/1997 | Porter |
| 5,656,016 A | 8/1997 | Ogden |
| 5,660,180 A | 8/1997 | Malinowski |
| 5,660,909 A | 8/1997 | Tachibana et al. |
| 5,665,076 A | 9/1997 | Roth |
| 5,681,296 A | 10/1997 | Ishida |
| 5,695,460 A | 12/1997 | Siegel et al. |
| 5,697,897 A | 12/1997 | Buchholtz et al. |
| 5,713,831 A | 2/1998 | Olsson |
| 5,713,848 A | 2/1998 | Dubrul et al. |
| 5,720,710 A | 2/1998 | Tachibana et al. |
| 5,724,976 A | 3/1998 | Hirama et al. |
| 5,725,494 A | 3/1998 | Brisken |
| 5,728,062 A | 3/1998 | Brisken |
| 5,733,315 A | 3/1998 | Burdette et al. |
| 5,735,811 A | 4/1998 | Brisken |
| 5,752,930 A | 5/1998 | Baudino et al. |
| 5,772,632 A | 6/1998 | Forman |
| 5,775,338 A | 7/1998 | Hastings |
| 5,779,673 A | 7/1998 | Roth |
| 5,807,395 A | 9/1998 | Mulier et al. |
| 5,817,021 A | 10/1998 | Reichenberger |
| 5,823,962 A | 10/1998 | Lerch et al. |
| 5,827,203 A | 10/1998 | Nita |
| 5,827,313 A | 10/1998 | Ream |
| 5,834,880 A | 11/1998 | Lewandowski et al. |
| 5,836,896 A | 11/1998 | Rosenschein |
| 5,836,940 A | 11/1998 | Gregory |
| 5,840,031 A | 11/1998 | Crowley |
| 5,842,994 A | 12/1998 | Tenhoff et al. |
| 5,846,218 A | 12/1998 | Brisken et al. |
| 5,876,345 A | 3/1999 | Eaton et al. |
| 5,908,445 A | 6/1999 | Whayne et al. |
| 5,916,192 A | 6/1999 | Nita et al. |
| 5,925,016 A | 7/1999 | Chornenky et al. |
| 5,928,186 A | 7/1999 | Homsma et al. |
| 5,931,805 A | 8/1999 | Brisken |
| 5,934,284 A | 8/1999 | Plaia et al. |
| 5,935,124 A | 8/1999 | Klumb et al. |
| 5,938,595 A | 8/1999 | Glass et al. |
| 5,941,868 A | 8/1999 | Kaplan et al. |
| 5,957,851 A | 9/1999 | Hossack |
| 5,957,882 A | 9/1999 | Nita et al. |
| 5,957,941 A | 9/1999 | Ream |
| 5,971,949 A | 10/1999 | Levin et al. |
| 5,976,120 A | 11/1999 | Chow et al. |
| 5,984,882 A | 11/1999 | Rosenschein et al. |
| 5,997,497 A | 12/1999 | Nita et al. |
| 6,001,069 A * | 12/1999 | Tachibana et al. ............ 601/2 |
| 6,004,069 A | 12/1999 | Sudbury |
| 6,004,269 A | 12/1999 | Crowley et al. |
| 6,024,703 A | 2/2000 | Zanelli et al. |
| 6,024,718 A | 2/2000 | Chen et al. |
| 6,027,515 A | 2/2000 | Cimino |
| 6,033,397 A | 3/2000 | Laufer et al. |
| 6,053,868 A | 4/2000 | Geistert et al. |
| 6,059,731 A | 5/2000 | Seward |
| 6,063,069 A | 5/2000 | Cragg et al. |
| 6,066,123 A | 5/2000 | Bednarski et al. |
| 6,078,830 A | 6/2000 | Levin et al. |
| 6,088,613 A | 7/2000 | Unger |
| 6,089,573 A | 7/2000 | Udagawa |
| 6,096,000 A | 8/2000 | Tachibana et al. |
| 6,110,098 A | 8/2000 | Renirie |
| 6,110,314 A | 8/2000 | Nix et al. |
| 6,113,546 A | 9/2000 | Suorsa |
| 6,113,558 A | 9/2000 | Rosenchein et al. |
| 6,113,570 A | 9/2000 | Siegel et al. |
| 6,117,101 A | 9/2000 | Diederich et al. |
| 6,120,454 A | 9/2000 | Suorsa |
| 6,135,971 A | 10/2000 | Hutchinson |
| 6,135,976 A | 10/2000 | Tachibana et al. |
| 6,149,596 A | 11/2000 | Bancroft |
| 6,149,599 A | 11/2000 | Schlesinger |
| 6,176,842 B1 | 1/2001 | Tachibana et al. |
| 6,196,973 B1 | 3/2001 | Lazenby |
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,231,516 B1 | 5/2001 | Keilman |
| 6,235,024 B1 | 5/2001 | Tu |
| 6,238,347 B1 | 5/2001 | Nix et al. |
| 6,270,460 B1 | 8/2001 | McCartan et al. |
| 6,277,077 B1 | 8/2001 | Brisken et al. |
| 6,283,920 B1 | 9/2001 | Eberle |
| 6,287,271 B1 | 9/2001 | Dubrul et al. |
| 6,296,610 B1 | 10/2001 | Schneider et al. |
| 6,296,619 B1 | 10/2001 | Brisken et al. |
| 6,299,597 B1 | 10/2001 | Buscemi et al. |
| 6,309,370 B1 | 10/2001 | Haim et al. |
| 6,312,402 B1 | 11/2001 | Hansmann |
| 6,361,500 B1 | 3/2002 | Masters |
| 6,361,554 B1 | 3/2002 | Brisken |
| 6,366,719 B1 | 4/2002 | Heath et al. |
| 6,372,498 B2 | 4/2002 | Newman et al. |
| 6,379,320 B1 | 4/2002 | Lafon et al. |
| 6,387,035 B1 | 5/2002 | Jung, Jr. et al. |
| 6,387,052 B1 | 5/2002 | Quinn |
| 6,391,042 B1 | 5/2002 | Cimino |
| 6,394,956 B1 | 5/2002 | Chandrasekaran et al. |
| 6,398,772 B1 | 6/2002 | Bond et al. |
| 6,398,792 B1 | 6/2002 | O'Connor |
| 6,416,740 B1 | 7/2002 | Unger |
| 6,423,026 B1 | 7/2002 | Gesswein et al. |
| 6,433,464 B2 | 8/2002 | Jones |
| 6,437,487 B1 | 8/2002 | Mohr, III |
| 6,454,737 B1 | 9/2002 | Nita et al. |
| 6,454,757 B1 | 9/2002 | Nita et al. |
| 6,456,863 B1 | 9/2002 | Levin |
| 6,461,314 B1 | 10/2002 | Pant et al. |
| 6,464,680 B1 | 10/2002 | Brisken et al. |
| 6,471,683 B2 | 10/2002 | Drasier et al. |
| 6,478,765 B2 | 11/2002 | Siegel et al. |
| 6,494,891 B1 | 12/2002 | Cornish et al. |
| 6,503,202 B1 | 1/2003 | Hossack et al. |
| 6,506,584 B1 | 1/2003 | Chandler et al. |
| 6,508,775 B2 | 1/2003 | McKenzie et al. |
| 6,511,478 B1 | 1/2003 | Burnside et al. |
| 6,524,251 B2 | 2/2003 | Rabiner et al. |
| 6,524,271 B2 | 2/2003 | Brisken et al. |
| 6,524,300 B2 | 2/2003 | Meglin |
| 6,537,224 B2 | 3/2003 | Mauchamp et al. |
| 6,537,306 B1 | 3/2003 | Burdette et al. |
| 6,542,767 B1 | 4/2003 | McNichols et al. |
| 6,551,337 B1 | 4/2003 | Rabiner et al. |
| 6,558,366 B1 | 5/2003 | Drasier et al. |
| 6,560,837 B1 | 5/2003 | Hodjat et al. |
| 6,561,998 B1 | 5/2003 | Roth |
| 6,562,021 B1 | 5/2003 | Derbin et al. |
| 6,565,552 B1 | 5/2003 | Barbut |
| 6,575,922 B1 | 6/2003 | Fearnside et al. |
| 6,575,956 B1 | 6/2003 | Brisken et al. |
| 6,579,277 B1 | 6/2003 | Rabiner et al. |
| 6,579,279 B1 | 6/2003 | Rabiner et al. |
| 6,582,392 B1 | 6/2003 | Bennett et al. |
| 6,585,763 B1 | 7/2003 | Keilman |
| 6,589,182 B1 | 7/2003 | Loftman |
| 6,589,253 B1 | 7/2003 | Cornish et al. |
| 6,599,288 B2 | 7/2003 | Maguire |
| 6,605,084 B2 | 8/2003 | Acker et al. |
| 6,607,502 B1 | 8/2003 | Maguire et al. |
| 6,623,444 B2 | 9/2003 | Babaev |
| 6,635,017 B1 | 10/2003 | Moehring et al. |
| 6,635,046 B1 | 10/2003 | Barbut |
| 6,645,150 B2 | 11/2003 | Angelsen et al. |
| 6,647,755 B2 | 11/2003 | Rabiner et al. |
| 6,652,547 B2 | 11/2003 | Rabiner et al. |
| 6,660,013 B2 | 12/2003 | Rabiner |
| 6,663,613 B1 | 12/2003 | Evans et al. |
| 6,676,626 B1 | 1/2004 | Bennett et al. |
| 6,682,502 B2 | 1/2004 | Bond et al. |
| 6,689,086 B1 | 2/2004 | Nita et al. |

(56) References Cited

U.S. PATENT DOCUMENTS

| | | |
|---|---|---|
| 6,695,781 B2 | 2/2004 | Rabiner et al. |
| 6,695,782 B2 | 2/2004 | Ranucci et al. |
| 6,695,785 B2 | 2/2004 | Brisken et al. |
| 6,711,953 B2 | 3/2004 | Hayashi et al. |
| 6,723,063 B1 * | 4/2004 | Zhang .................... A61M 5/14 604/22 |
| 6,723,064 B2 | 4/2004 | Babaev |
| 6,726,698 B2 | 4/2004 | Cimino |
| 6,730,048 B1 | 5/2004 | Hare et al. |
| 6,733,451 B2 | 5/2004 | Rabiner et al. |
| 6,740,040 B1 | 5/2004 | Mandrusov et al. |
| 6,767,345 B2 | 6/2004 | St. Germain et al. |
| 6,758,857 B2 | 7/2004 | Cioanta |
| 6,824,515 B2 | 11/2004 | Suorsa et al. |
| 6,824,575 B1 | 11/2004 | Otomo et al. |
| 6,830,577 B2 | 12/2004 | Nash et al. |
| 6,849,062 B2 | 2/2005 | Kantor |
| 6,855,123 B2 | 2/2005 | Nita |
| 6,866,670 B2 | 3/2005 | Rabiner et al. |
| 6,905,505 B2 | 6/2005 | Dodson, Jr. et al. |
| 6,921,371 B2 | 7/2005 | Wilson |
| 6,929,633 B2 | 8/2005 | Evans et al. |
| 6,942,620 B2 | 9/2005 | Nita et al. |
| 6,942,677 B2 | 9/2005 | Nita et al. |
| 6,945,937 B2 | 9/2005 | Culp et al. |
| 6,958,040 B2 | 10/2005 | Oliver |
| 6,979,293 B2 | 12/2005 | Hansmann et al. |
| 6,985,771 B2 | 1/2006 | Fischell et al. |
| 7,077,820 B1 | 7/2006 | Kadziauskas et al. |
| 7,089,063 B2 | 8/2006 | Lesh et al. |
| 7,137,963 B2 | 11/2006 | Nita et al. |
| 7,141,044 B2 | 11/2006 | Gentsler |
| 7,166,098 B1 | 1/2007 | Steward et al. |
| 7,186,246 B2 | 3/2007 | Bennett et al. |
| 7,220,233 B2 | 5/2007 | Nita et al. |
| 7,220,239 B2 | 5/2007 | Wilson et al. |
| 7,309,334 B2 | 12/2007 | von Hoffmann |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,413,556 B2 | 8/2008 | Zhang et al. |
| 7,503,895 B2 | 3/2009 | Rabiner et al. |
| 7,540,852 B2 | 6/2009 | Nita et al. |
| 7,567,016 B2 | 7/2009 | Lu et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,648,478 B2 | 1/2010 | Soltani et al. |
| 7,715,908 B2 | 5/2010 | Moran et al. |
| 7,727,178 B2 | 6/2010 | Wilson |
| 7,758,509 B2 | 7/2010 | Angelsen et al. |
| 7,771,372 B2 | 8/2010 | Wilson |
| 7,774,933 B2 | 8/2010 | Wilson et al. |
| 7,789,830 B2 | 9/2010 | Fujita et al. |
| 7,818,854 B2 | 10/2010 | Wilson |
| 7,828,754 B2 | 11/2010 | Abe et al. |
| 7,828,762 B2 | 11/2010 | Wilson |
| 7,862,576 B2 * | 1/2011 | Gurm ..................... 606/194 |
| 7,901,359 B2 | 3/2011 | Mandrusov et al. |
| 7,914,509 B2 | 3/2011 | Bennett et al. |
| 8,012,092 B2 | 9/2011 | Powers et al. |
| 8,062,566 B2 | 11/2011 | Nita et al. |
| 8,123,789 B2 | 2/2012 | Khanna |
| 8,152,753 B2 | 4/2012 | Nita et al. |
| 8,167,831 B2 | 5/2012 | Wilson |
| 8,192,363 B2 | 6/2012 | Soltani et al. |
| 8,696,612 B2 | 4/2014 | Wilson et al. |
| 8,740,835 B2 | 6/2014 | Soltani et al. |
| 8,764,700 B2 | 7/2014 | Zhang et al. |
| 8,819,928 B2 | 9/2014 | Nix et al. |
| 9,044,568 B2 | 6/2015 | Wilcox et al. |
| 9,107,590 B2 | 8/2015 | Hansmann et al. |
| 9,192,566 B2 | 11/2015 | Soltani et al. |
| 9,415,242 B2 | 8/2016 | Wilson et al. |
| 10,080,878 B2 | 9/2018 | Wilson et al. |
| 10,092,742 B2 | 10/2018 | Gentstler et al. |
| 10,182,833 B2 | 1/2019 | Soltani et al. |
| 10,188,410 B2 | 1/2019 | Soltani et al. |
| 2001/0000791 A1 | 5/2001 | Suorsa et al. |
| 2001/0007861 A1 | 7/2001 | Newman |
| 2001/0007940 A1 | 7/2001 | Tu et al. |
| 2001/0025190 A1 | 9/2001 | Weber et al. |
| 2001/0037106 A1 | 11/2001 | Shadduck |
| 2001/0039419 A1 | 11/2001 | Francischelli et al. |
| 2001/0041842 A1 | 11/2001 | Eberle |
| 2002/0000763 A1 | 1/2002 | Jones |
| 2002/0019644 A1 | 2/2002 | Hastings |
| 2002/0032394 A1 | 3/2002 | Brisken et al. |
| 2002/0045890 A1 | 4/2002 | Celliers et al. |
| 2002/0052620 A1 | 5/2002 | Barbut |
| 2002/0068869 A1 | 6/2002 | Brisken et al. |
| 2002/0082238 A1 | 6/2002 | Newman et al. |
| 2002/0087083 A1 | 7/2002 | Nix |
| 2002/0099292 A1 | 7/2002 | Brisken et al. |
| 2002/0123787 A1 | 9/2002 | Weiss |
| 2002/0133111 A1 | 9/2002 | Shadduck |
| 2002/0077550 A1 | 10/2002 | Rabiner et al. |
| 2002/0188276 A1 | 12/2002 | Evan et al. |
| 2002/0193708 A1 | 12/2002 | Thompson et al. |
| 2003/0036705 A1 | 2/2003 | Hare et al. |
| 2003/0040501 A1 | 2/2003 | Newman et al. |
| 2003/0050662 A1 | 3/2003 | Don Michael |
| 2003/0065263 A1 | 4/2003 | Hare et al. |
| 2003/0069525 A1 | 4/2003 | Brisken et al. |
| 2003/0083608 A1 | 5/2003 | Evans et al. |
| 2003/0109812 A1 | 6/2003 | Cort et al. |
| 2003/0135262 A1 | 7/2003 | Dretler et al. |
| 2003/0163147 A1 * | 8/2003 | Rabiner et al. ............. 606/159 |
| 2003/0236539 A1 | 12/2003 | Rabiner et al. |
| 2004/0001809 A1 | 1/2004 | Brisken et al. |
| 2004/0015122 A1 | 1/2004 | Zhang et al. |
| 2004/0019318 A1 | 1/2004 | Wilson et al. |
| 2004/0024393 A1 | 2/2004 | Nita et al. |
| 2004/0039311 A1 | 2/2004 | Nita et al. |
| 2004/0049148 A1 | 3/2004 | Rodriguez et al. |
| 2004/0059313 A1 | 3/2004 | Anderson et al. |
| 2004/0068189 A1 | 4/2004 | Wilson et al. |
| 2004/0097996 A1 | 5/2004 | Hare et al. |
| 2004/0122354 A1 * | 6/2004 | Semba ..................... 604/66 |
| 2004/0133232 A1 * | 7/2004 | Rosenbluth et al. ......... 606/200 |
| 2004/0138570 A1 | 7/2004 | Nita et al. |
| 2004/0162571 A1 | 8/2004 | Rabiner et al. |
| 2004/0171981 A1 | 9/2004 | Buffen et al. |
| 2004/0220514 A1 | 11/2004 | Cafferata |
| 2004/0236350 A1 | 11/2004 | Bolduc et al. |
| 2004/0243062 A1 | 12/2004 | Henry |
| 2004/0255957 A1 | 12/2004 | Cafferata |
| 2004/0265393 A1 | 12/2004 | Unger et al. |
| 2005/0021063 A1 | 1/2005 | Hall et al. |
| 2005/0043629 A1 | 2/2005 | Rabiner et al. |
| 2005/0043753 A1 | 2/2005 | Rabiner et al. |
| 2005/0124877 A1 | 6/2005 | Nita et al. |
| 2005/0137520 A1 | 6/2005 | Rule et al. |
| 2005/0187513 A1 | 8/2005 | Rabiner et al. |
| 2005/0187514 A1 | 8/2005 | Rabiner et al. |
| 2005/0192558 A1 | 9/2005 | Soltani et al. |
| 2005/0197619 A1 | 9/2005 | Rule et al. |
| 2005/0209578 A1 | 9/2005 | Christian Evans et al. |
| 2005/0215942 A1 | 9/2005 | Abrahamson et al. |
| 2005/0215946 A1 | 9/2005 | Hansmann et al. |
| 2005/0216044 A1 | 9/2005 | Hong |
| 2005/0096669 A1 | 10/2005 | Rabiner et al. |
| 2005/0256410 A1 | 11/2005 | Rabiner et al. |
| 2005/0113688 A1 | 12/2005 | Nita et al. |
| 2005/0119679 A1 | 12/2005 | Rabiner et al. |
| 2005/0288695 A1 | 12/2005 | Jenson et al. |
| 2006/0069303 A1 | 3/2006 | Couvillon |
| 2006/0106308 A1 | 5/2006 | Hansmann et al. |
| 2006/0116610 A1 | 6/2006 | Hare et al. |
| 2006/0173387 A1 | 8/2006 | Hansmann et al. |
| 2006/0184070 A1 | 8/2006 | Hansmann et al. |
| 2007/0005121 A1 | 1/2007 | Khanna |
| 2007/0037119 A1 | 2/2007 | Pal et al. |
| 2007/0038158 A1 | 2/2007 | Nita et al. |

(56) References Cited

U.S. PATENT DOCUMENTS

| | | |
|---|---|---|
| 2007/0066978 A1 | 3/2007 | Schafer et al. |
| 2007/0112268 A1 | 5/2007 | Zhang et al. |
| 2007/0225619 A1 | 9/2007 | Rabiner et al. |
| 2007/0239027 A1 | 10/2007 | Nita |
| 2007/0255252 A1* | 11/2007 | Mehta .................. 604/508 |
| 2007/0265560 A1 | 11/2007 | Soltani et al. |
| 2008/0045865 A1 | 2/2008 | Kislev |
| 2008/0065014 A1 | 3/2008 | McCrystle et al. |
| 2008/0109029 A1* | 5/2008 | Gurm .................. 606/194 |
| 2008/0146918 A1 | 6/2008 | Magnin et al. |
| 2008/0154181 A1 | 6/2008 | Khanna |
| 2008/0167602 A1 | 7/2008 | Nita et al. |
| 2008/0171965 A1 | 7/2008 | Soltani et al. |
| 2008/0172067 A1 | 7/2008 | Nita et al. |
| 2008/0194954 A1 | 8/2008 | Matsunaga et al. |
| 2008/0221506 A1 | 9/2008 | Rodriguez et al. |
| 2008/0262350 A1 | 9/2008 | Abrahamson et al. |
| 2008/0306499 A1 | 12/2008 | Katoh et al. |
| 2008/0319355 A1 | 12/2008 | Nita |
| 2008/0319376 A1* | 12/2008 | Wilcox ............ A61B 17/2202 601/2 |
| 2009/0018472 A1 | 1/2009 | Soltani et al. |
| 2009/0073455 A1 | 3/2009 | Onimura |
| 2009/0105597 A1 | 4/2009 | Abraham |
| 2009/0112150 A1 | 4/2009 | Unger et al. |
| 2009/0209900 A1 | 8/2009 | Carmeli et al. |
| 2009/0216246 A1 | 8/2009 | Nita et al. |
| 2009/0221902 A1* | 9/2009 | Myhr .................. 600/411 |
| 2010/0010393 A1 | 1/2010 | Duffy et al. |
| 2010/0022920 A1 | 1/2010 | Nita et al. |
| 2010/0022944 A1 | 1/2010 | Wilcox |
| 2010/0023036 A1 | 1/2010 | Nita et al. |
| 2010/0023037 A1 | 1/2010 | Nita et al. |
| 2010/0049209 A1 | 2/2010 | Nita et al. |
| 2010/0063413 A1 | 3/2010 | Volz |
| 2010/0063414 A1 | 3/2010 | Volz |
| 2010/0081934 A1 | 4/2010 | Hansmann et al. |
| 2010/0204582 A1 | 8/2010 | Lu |
| 2010/0210940 A1 | 8/2010 | Bradley et al. |
| 2010/0222715 A1 | 9/2010 | Nita |
| 2010/0256616 A1 | 10/2010 | Katoh et al. |
| 2010/0262215 A1 | 10/2010 | Gertner |
| 2010/0292685 A1 | 11/2010 | Katoh et al. |
| 2011/0160621 A1 | 6/2011 | Nita |
| 2011/0201974 A1 | 8/2011 | Hansmann et al. |
| 2011/0288449 A1 | 11/2011 | Schenkengel |
| 2011/0313328 A1 | 12/2011 | Nita |
| 2011/0319927 A1 | 12/2011 | Nita |
| 2012/0016272 A1 | 1/2012 | Nita et al. |
| 2012/0041307 A1 | 2/2012 | Patel et al. |
| 2012/0059285 A1 | 3/2012 | Soltani et al. |
| 2012/0078140 A1 | 3/2012 | Nita |
| 2012/0123273 A1 | 5/2012 | Okuno et al. |
| 2012/0172795 A1 | 7/2012 | Sandhu et al. |
| 2012/0172858 A1 | 7/2012 | Harrison et al. |
| 2012/0179073 A1 | 7/2012 | Nita |
| 2012/0197277 A1 | 8/2012 | Stinis |
| 2012/0289889 A1 | 11/2012 | Genstler et al. |
| 2012/0330141 A1 | 12/2012 | Brown et al. |
| 2014/0046313 A1 | 2/2014 | Pederson et al. |
| 2014/0210631 A1 | 7/2014 | Zavis |
| 2014/0236118 A1 | 8/2014 | Unser et al. |
| 2014/0249453 A1 | 9/2014 | Wilson |
| 2014/0343483 A1 | 11/2014 | Zhang et al. |
| 2015/0173673 A1 | 6/2015 | Toth et al. |
| 2016/0262777 A1 | 9/2016 | Stigall et al. |
| 2016/0361528 A1 | 12/2016 | Kanz et al. |
| 2019/0091458 A1 | 3/2019 | Wilson et al. |
| 2019/0099591 A1 | 4/2019 | Genstler et al. |

FOREIGN PATENT DOCUMENTS

| | | |
|---|---|---|
| EP | 0 629 382 | 12/1994 |
| EP | 0 744 189 | 11/1996 |
| EP | 0 746 245 | 12/1996 |
| EP | 1 090 658 | 4/2001 |
| JP | 02-180275 | 7/1990 |
| WO | WO 92/000113 | 1/1992 |
| WO | WO 95/001751 | 1/1995 |
| WO | WO 95/005866 | 3/1995 |
| WO | WO 95/026777 | 10/1995 |
| WO | WO 96/004955 | 2/1996 |
| WO | WO 96/027341 | 9/1996 |
| WO | WO 96/029935 | 10/1996 |
| WO | WO 96/036286 | 11/1996 |
| WO | WO 97/019645 | 6/1997 |
| WO | WO 98/011826 | 3/1998 |
| WO | WO 89/004142 | 5/1998 |
| WO | WO 98/018391 | 5/1998 |
| WO | WO 98/048711 | 11/1998 |
| WO | WO 98/056462 | 12/1998 |
| WO | WO 99/032184 | 7/1999 |
| WO | WO 99/033500 | 7/1999 |
| WO | WO 99/034858 | 7/1999 |
| WO | WO 99/039647 | 8/1999 |
| WO | WO 99/044512 | 9/1999 |
| WO | WO 00/000095 | 1/2000 |
| WO | WO 00/038580 | 7/2000 |
| WO | WO 00/069341 | 11/2000 |
| WO | WO 01/054754 | 8/2001 |
| WO | WO 01/087174 | 11/2001 |
| WO | WO 01/095788 | 12/2001 |
| WO | WO 02/013678 | 2/2002 |
| WO | WO 02/015803 | 2/2002 |
| WO | WO 02/015804 | 2/2002 |
| WO | WO 03/051208 | 6/2003 |
| WO | WO 2005/027756 | 3/2005 |
| WO | WO 2005/084552 | 9/2005 |
| WO | WO 2005/084553 | 9/2005 |
| WO | WO 2008/052186 | 5/2008 |
| WO | WO 2015/074036 | 5/2015 |
| WO | WO 2016/201136 | 12/2016 |

OTHER PUBLICATIONS

Lin et al., "Comparison of Percutaneous Ultrasound-Accelerated Thrombolysis versus Catheter-Directed Thrombolysis in Patients with Acute Massive Pulmonary Embolism," Vascular, 2009, vol. 17, No. 3, pp. S137-S147.

Hynynen et al.; "Small Cylindrical Ultrasound Sources for Induction of Hyperthermia via Body Cavities or Interstitial Implants", Arizona Cancer Center and Department of Radiation Oncology, University of Arizona Health Sciences Center; vol. 9, No. 2, 1993, pp. 263-274.

Lee et al.; "Arrays of Multielement Ultrasound Applicators for Interstitial Hyperthermia"; IEEE Transactions on biomedical Engineering; vol. 46, No. 7, Jul. 1999, pp. 880-890.

Schäfer et al., "Influence of Ultrasound Operating Parameters on Ultrasound-Induced Thrombolysis In Vitro," Ultrasound in Medicine and Biology, vol. 31, No. 6, Mar. 2005, pp. 841-847.

Tsetis et al., "Potential Benefits From Heating the High-Dose Rtpa Boluses Used in Catheter-Directed Thrombolysis for Acute/Subacute Lower Limb Ischemia", Journal of Endovascular Therapy, 2003, vol. 10, pp. 739-744.

* cited by examiner

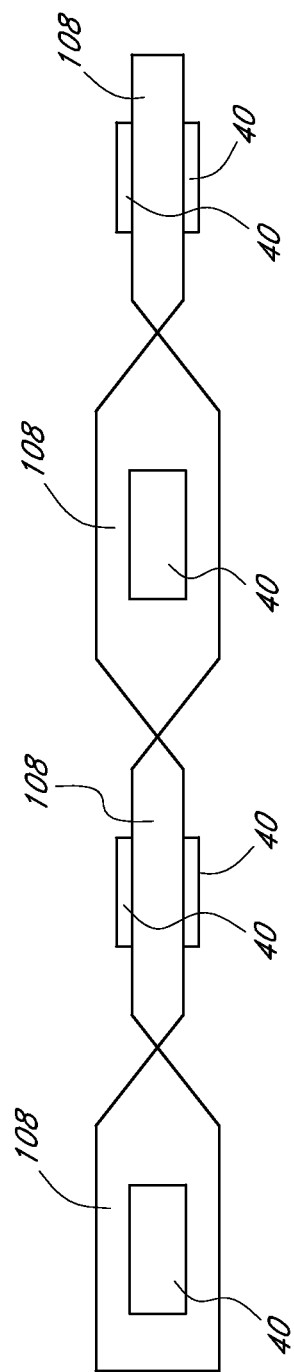

FIG. 16

ULTRASOUND SYSTEM

CROSS-REFERENCE TO RELATED APPLICATIONS

This application claims the priority benefit to U.S. Provisional Application No. 61/579,545, filed Dec. 22, 2011, and U.S. Provisional Application No. 61/485,022, filed May 11, 2011, the entire contents of which are hereby incorporated by reference herein.

FIELD OF THE APPLICATION

The present invention relates generally to ultrasound systems, and more specifically to treating pulmonary embolism using an ultrasound systems.

BACKGROUND

Ultrasonic energy had been used to enhance the intravascular delivery and/or effect of various therapeutic compounds. In one system, ultrasound catheters are used to deliver ultrasonic energy and therapeutic compounds to a treatment site within a patient's vasculature. Such ultrasound catheters can comprise an elongate member configured to be advanced through a patient's vasculature and an ultrasound assembly that is positioned near a distal end portion of the elongate member. The ultrasound assembly is configured to emit ultrasonic energy. Such ultrasound catheters can include a fluid delivery lumen that is used to deliver the therapeutic compound to the treatment site. In this manner, ultrasonic energy is delivered to the treatment site to enhance the effect and/or delivery of the therapeutic compound.

For example, ultrasound catheters have been successfully used to treat human blood vessels that have become occluded by plaque, thrombi, emboli or other substances that reduce the blood carrying capacity of the vessel. See, for example, U.S. Pat. No. 6,001,069. To remove the occlusion, the ultrasound catheter is advanced through the patient's vasculature to deliver a therapeutic compound containing dissolution compounds directly to the occlusion. To enhance the effect and/or delivery of the therapeutic compound, ultrasonic energy is emitted into the therapeutic compound and/or the surrounding tissue at the treatment site. In other applications, ultrasound catheters are used for other purposes, such as for the delivery and activation of light activated drugs. See, for example, U.S. Pat. No. 6,176,842.

Pulmonary embolisms (PE) are caused when a large blood clot obstructs the major blood vessels leading from the heart to the lungs. The victim's heat can be suddenly overwhelmed with the task of pushing blood bas this obstruction. About 5% of PE's are classified as massive and can result in rapid heart failure, shock and death without immediate therapy. Such massive PE's have traditionally been treated by a large dose of clot-dissolving drug (i.e., a thrombolytic). However, such treatment can result in unintended bleeding and even fatalities. Up to 40% of PE's are less critical obstructions, often called sub-massive PE. Current treatment protocols include treatment with anti-coagulant medication. Such treatments do not remove the clot but simply prevent the clot from growing larger. Recent studies suggest that failure to remove these sub-massive clots may have long-term adverse consequences including recurrent PE, chronic pulmonary hypertension and death.

SUMMARY

One aspect comprises a method for treating a patient having pulmonary embolism, the method comprising: providing an ultrasound catheter, the ultrasound catheter comprising an tubular body having a proximal portion and a distal portion, the distal portion comprising an ultrasound energy delivery section, wherein the elongate body comprises a central lumen and at least one fluid delivery lumen; providing an elongate inner core comprising at least one ultrasound radiating member; advancing the distal portion of the ultrasound catheter to a treatment site in the patient's pulmonary artery; positioning the elongate inner core in the central lumen; delivering a thrombolytic drug to the treatment site through the at least one fluid delivery lumen; and emitting ultrasonic energy to thereby promote diffusion of the thrombolytic drug at the treatment site.

BRIEF DESCRIPTION OF THE DRAWINGS

Exemplary embodiments of the cavitation promoting systems and methods disclosed herein are illustrated in the accompanying drawings, which are for illustrative purposes only. The drawings comprise the following figures, in which like numerals indicate like parts.

FIG. 7D is a side view of an ultrasound assembly center wire twisted into a helical configuration.

FIG. 16 is a schematic wiring diagram illustrating a technique for electrically connecting groups of ultrasound radiating members to form an ultrasound assembly.

DETAILED DESCRIPTION

Figure 1:
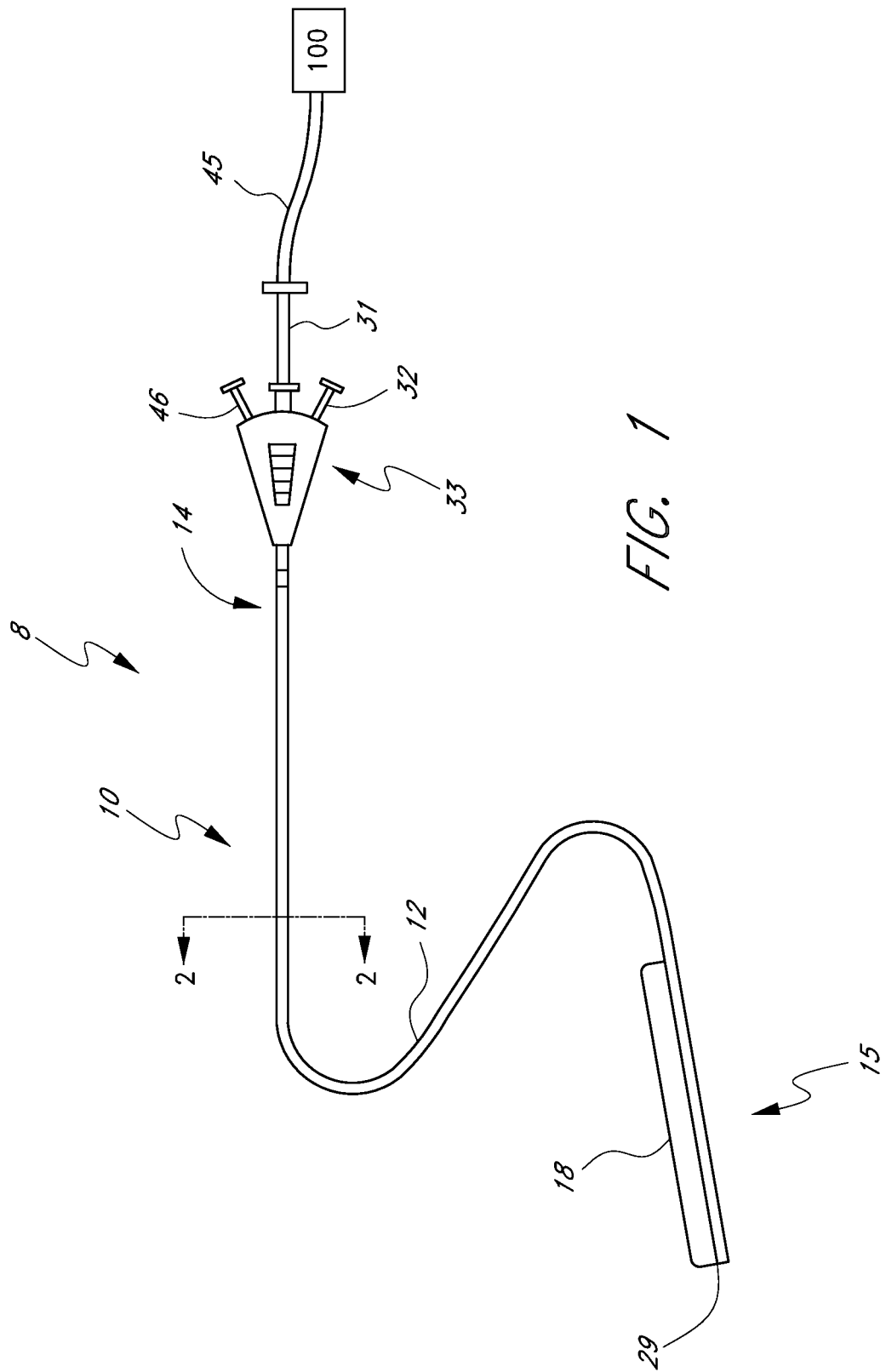
FIG. 1 is a schematic illustration of certain features of an example ultrasonic catheter.

As used herein, the term "ultrasonic energy" is used broadly, includes its ordinary meaning, and further includes mechanical energy transferred through pressure or compression waves with a frequency greater than about 20 kHz. Ultrasonic energy waves have a frequency between about 500 kHz and about 20 MHz in one example embodiment, between about 1 MHz and about 3 MHz in another example embodiment, of about 3 MHz in another example embodiment, and of about 2 MHz in another example embodiment. As used herein, the term "catheter" is used broadly, includes its ordinary meaning, and further includes an elongate flexible tube configured to be inserted into the body of a patient, such as into a body part, cavity, duct or vessel.

As used herein, the term "therapeutic compound" refers broadly, without limitation, and in addition to its ordinary meaning, to a drug, medicament, dissolution compound, genetic material or any other substance capable of effecting physiological functions. Additionally, a mixture including substances such as these is also encompassed within this definition of "therapeutic compound". Examples of therapeutic compounds include thrombolytic compounds, anti-thrombosis compounds, and other compounds used in the treatment of vascular occlusions and/or blood clots, including compounds intended to prevent or reduce clot formation, neuroprotective agents, anti-apoptotic agents, and neurotoxin scavenging agents. Exemplary therapeutic compounds include, but are not limited to, heparin, urokinase, streptokinase, tPA, rtPA, BB-10153 (manufactured by British Biotech, Oxford, UK), plasmin, IIbIIa inhibitors, desmoteplase, caffeinol, deferoxamine, and factor VIIa. Therapeutic compound can also include drugs and compounds for treating cancer and/or tumors.

As expounded herein, ultrasonic energy is often used to enhance the delivery and/or effect of a therapeutic compound. For example, in the context of treating vascular occlusions, ultrasonic energy has been shown to increase enzyme mediated thrombolysis by enhancing the delivery of thrombolytic agents into a thrombus, where such agents lyse the thrombus by degrading the fibrin that forms the thrombus. The thrombolytic activity of the agent is enhanced in the presence of ultrasonic energy in the thrombus. However, it should be appreciated that the embodiments disclosed herein should not be limited to the mechanism by which the ultrasound enhances treatment unless otherwise stated. In other applications, ultrasonic energy has also been shown to enhance transfection of gene-based drugs into cells, and augment transfer of chemotherapeutic drugs into tumor cells. Ultrasonic energy delivered from within a patient's body has been found to be capable of producing non-thermal effects that increase biological tissue permeability to therapeutic compounds by up to or greater than an order of magnitude.

Use of an ultrasound catheter to deliver ultrasonic energy and a therapeutic compound directly to the treatment site mediates or overcomes many of the disadvantages associated with systemic drug delivery, such as low efficiency, high therapeutic compound use rates, and significant side effects caused by high doses. Local therapeutic compound delivery has been found to be particularly advantageous in the context of thrombolytic therapy, chemotherapy, radiation therapy, and gene therapy, as well as in applications calling for the delivery of proteins and/or therapeutic humanized antibodies. However, it should be appreciated that in certain arrangements the ultrasound catheter can also be used in combination with systemic drug delivery instead or in addition to local drug deliver. In addition, local drug delivery can be accomplished through the use of a separate device (e.g., catheter).

As will be described below, the ultrasound catheter can include one or more one or more ultrasound radiating members positioned therein. Used herein, the term "ultrasound radiating element" or "ultrasound or ultrasonic element" refers broadly, without limitation, and in addition to its ordinary meaning, to any apparatus capable of producing ultrasonic energy. An ultrasonic transducer, which converts electrical energy into ultrasonic energy, is an example of an ultrasound radiating element. An exemplary ultrasonic transducer capable of generating ultrasonic energy from electrical energy is a piezoelectric ceramic oscillator. Piezoelectric ceramics typically comprise a crystalline material, such as quartz, that changes shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating element, and the ultrasonic energy can be transmitted, via, for example, a wire that is coupled to the ultrasound radiating element. In such embodiments, a "transverse wave" can be generated along the wire. As used herein is a wave propagated along the wire in which the direction of the disturbance at each point of the medium is perpendicular to the wave vector. Some embodiments, such as embodiments incorporating a wire coupled to an ultrasound radiating element for example, are capable of generating transverse waves. See e.g., U.S. Pat. Nos. 6,866,670, 6,660,013 and 6,652,547, the entirety of which are hereby incorporated by reference herein. Other embodiments without the wire can also generate transverse waves along the body of the catheter.

With reference to the illustrated embodiments, FIG. 1 illustrates one embodiment of an ultrasound system 8 for treatment of a pulmonary embolism. The system 8 includes an ultrasound catheter 10 and a control system 100. As will be explained in detail below, in one embodiment, the catheter is configured to be introduced into the patient's the major blood vessels leading from the heart to the lungs (e.g., the pulmonary artery). In one embodiment of use, femoral venous access may be used to place the catheter 10 into such vessels. In such embodiments, the catheter 10 can be advanced through femoral access site, through the heart and into the pulmonary artery. The dimensions of the catheter 10 are adjusted based on the particular application for which the catheter 10 is to be used.

In the illustrated arrangement, the ultrasonic catheter 10 can comprise a multi-component, elongate flexible tubular body 12 having a proximal region 14 and a distal region 15. The tubular body 12 includes a flexible energy delivery section 18 located in the distal region 15 of the catheter 10. The tubular body 12 and other components of the catheter 10 are manufactured in accordance with a variety of techniques. Suitable materials and dimensions are selected based on the natural and anatomical dimensions of the treatment site and on the desired percutaneous access site.

For example, in a one embodiment the proximal region 14 of the tubular body 12 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the proximal region 14 of the tubular body 12 is reinforced by braiding, mesh or other constructions to provide increased kink resistance and pushability. For example, in certain embodiments nickel titanium or stainless steel wires are placed along or incorporated into the tubular body 12 to reduce kinking.

The energy delivery section 18 of the tubular body 12 optionally comprises a material that (a) is thinner than the material comprising the proximal region 14 of the tubular body 12, or (b) has a greater acoustic transparency than the material comprising the proximal region 14 of the tubular body 12. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 is formed from the same material or a material of the same thickness as the proximal region 18.

One or more fluid delivery lumens can be incorporated into the tubular body 12. For example, in one embodiment a central lumen passes through the tubular body 12. The central lumen extends through the length of the tubular body 12, and is coupled to a distal exit port 29 and a proximal access port 31. The proximal access port 31 forms part of the backend hub 33, which is attached to the proximal region 14 of the catheter 10. The backend hub 33 optionally further comprises cooling fluid fitting 46, which is hydraulically connected to a lumen within the tubular body 12. The backend hub 33 also optionally comprises a therapeutic compound inlet port 32, which is hydraulically connected to a lumen within the tubular body 12. The therapeutic compound inlet port 32 is optionally also hydraulically coupled to a source of therapeutic compound via a hub such as a Luer fitting.

The catheter 10 can include one or more ultrasound radiating members positioned therein. For example, in certain embodiments an ultrasound radiating member can fixed within and/or incorporated into the energy delivery section 18 of the tubular body, while in other embodiments a plurality of ultrasound radiating members are fixed to an assembly that is passed into the central lumen. In either case, the one or more ultrasound radiating members are electrically coupled to a control system 100 via cable 45. In one embodiment, the outer surface of the energy delivery 18 section can include a cavitation promoting surface configured to enhance/promote cavitation at the treatment site.

Figure 2:
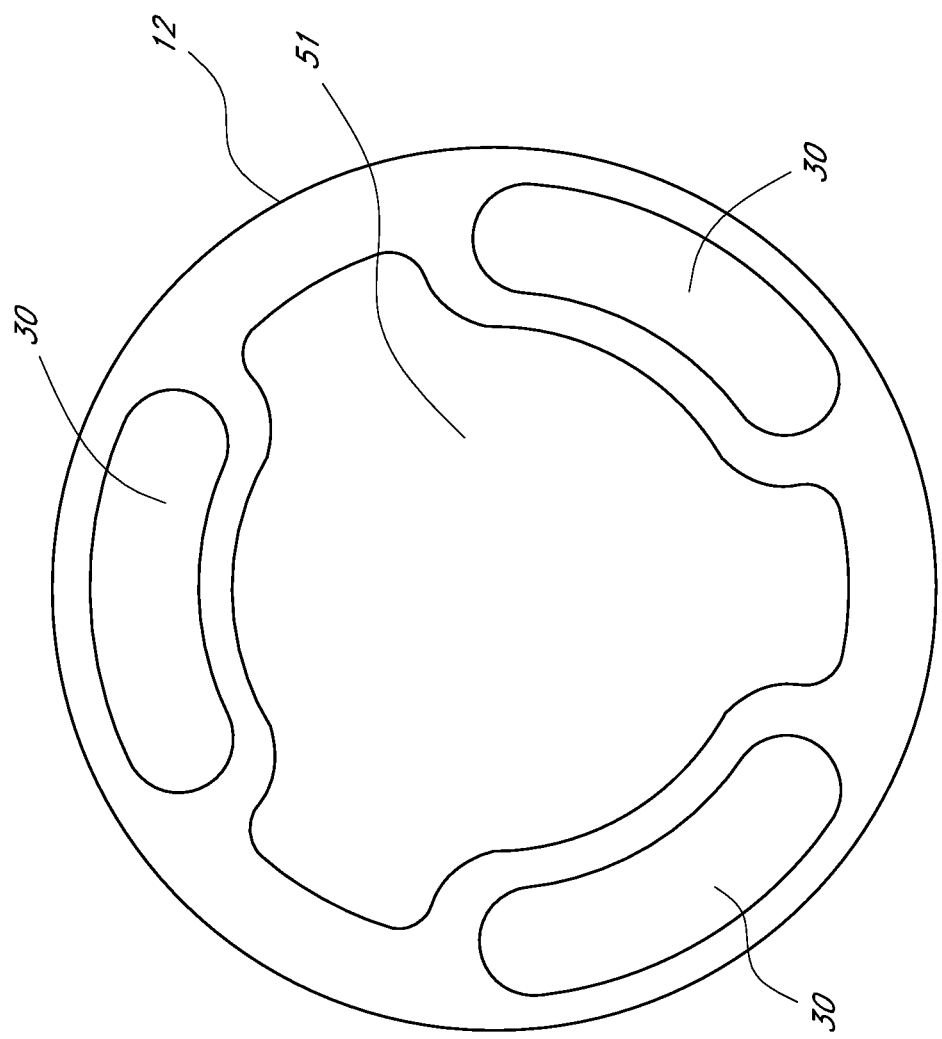
FIG. 2 is a cross-sectional view of the ultrasonic catheter of FIG. 1 taken along line 2-2.

With reference to FIG. 2-10, one arrangement of the energy delivery section 18 and other portions of the catheter 10 described above. FIG. 2 illustrates a cross section of the tubular body 12 taken along line 2-2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. The arrangement of the fluid delivery lumens 30 provides a hollow central lumen 51 passing through the tubular body 12. The cross-section of the tubular body 12, as illustrated in FIG. 2, can be substantially constant along the length of the catheter 10. Thus, in such embodiments, substantially the same cross-section is present in both the proximal region 14 and the distal region 15 of the catheter 10, including the energy delivery section 18.

In certain embodiments, the central lumen 51 has a minimum diameter greater than about 0.030 inches. In another embodiment, the central lumen 51 has a minimum diameter greater than about 0.037 inches. In one embodiment, the fluid delivery lumens 30 have dimensions of about 0.026 inches wide by about 0.0075 inches high, although other dimensions may be used in other applications.

As described above, the central lumen 51 can extend through the length of the tubular body 12. As illustrated in FIG. 1, the central lumen 51 can have a distal exit port 29 and a proximal access port 31. The proximal access port 31 forms part of the backend hub 33, which is attached to the proximal region 14 of the catheter 10. The backend hub can further comprise a cooling fluid fitting 46, which is hydraulically connected to the central lumen 51. The backend hub 33 can also comprise a therapeutic compound inlet port 32, which is in hydraulic connection with the fluid delivery lumens 30, and which can be hydraulically coupled to a source of therapeutic compound via a hub such as a Luer fitting.

Figure 3:
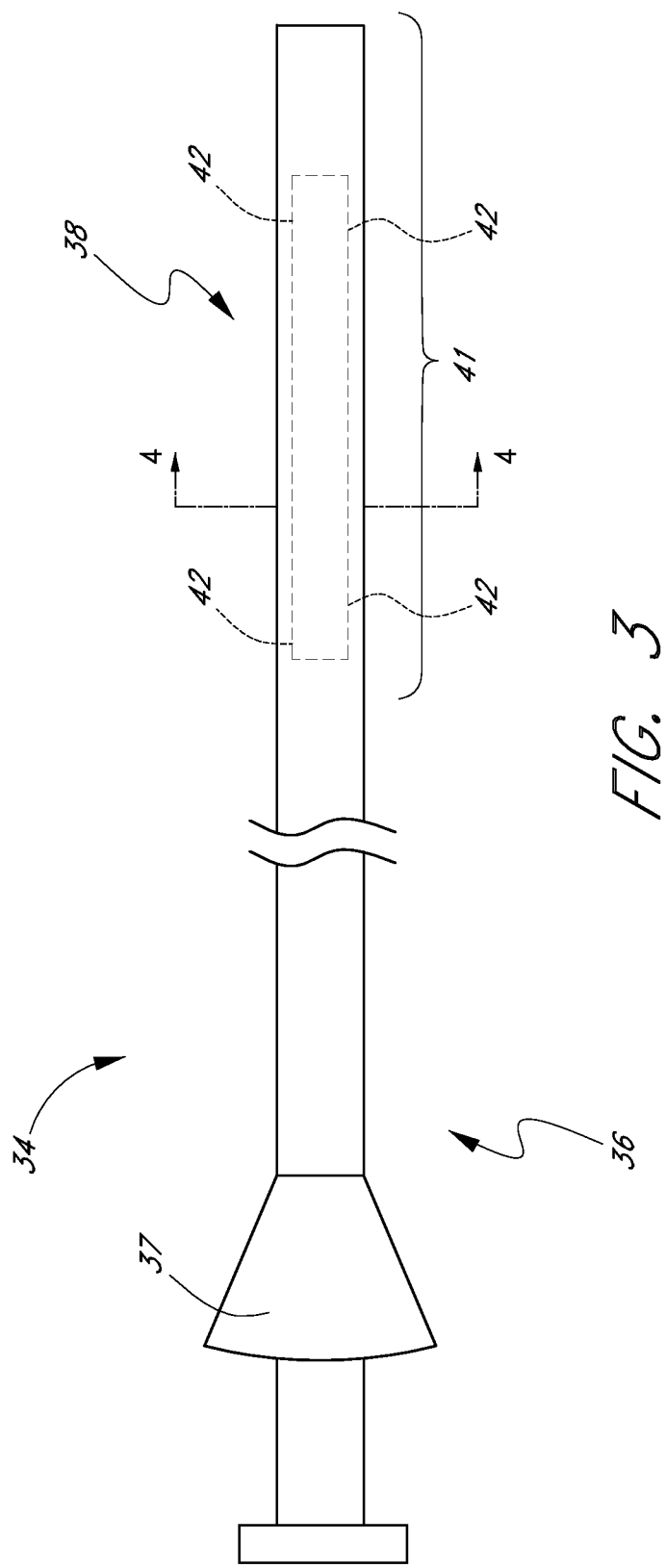
FIG. 3 is a schematic illustration of an elongate inner core configured to be positioned within the central lumen of the catheter illustrated in FIG. 2.

The central lumen 51 can receive an elongate inner core 34 of which an embodiment is illustrated in FIG. 3. The elongate inner core 34 can include a proximal region 36 and a distal region 38. Proximal hub 37 is fitted on the inner core 34 at one end of the proximal region 36. One or more ultrasound radiating members are positioned within an inner core energy delivery section 41 located within the distal region 38. The ultrasound radiating members 40 form an ultrasound assembly 42, which will be described in detail below.

Figure 4:
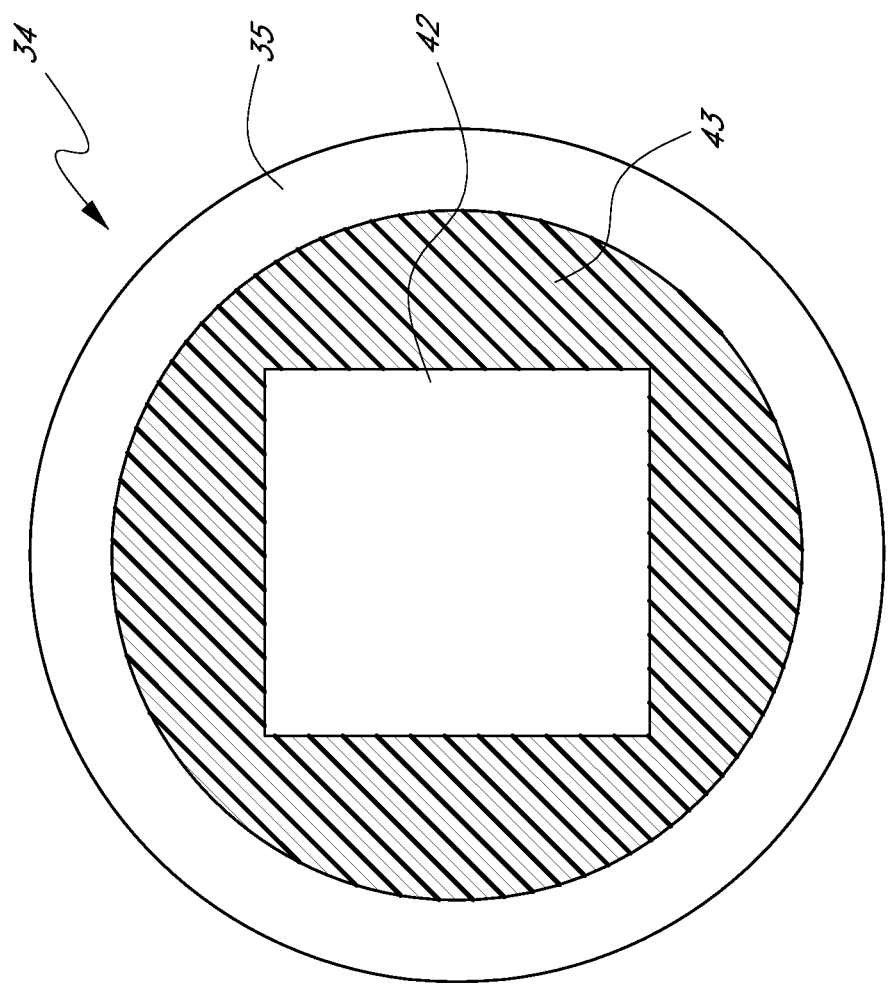
FIG. 4 is a cross-sectional view of the elongate inner core of FIG. 3 taken along line 4-4.

As shown in the cross-section illustrated in FIG. 4, which is taken along lines 4-4 in FIG. 3, the inner core 34 can have a cylindrical shape, with an outer diameter that permits the inner core 34 to be inserted into the central lumen 51 of the tubular body 12 via the proximal access port 31. Suitable outer diameters of the inner core 34 include, but are not limited to, about 0.010 inches to about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 can include a cylindrical outer body 35 that houses the ultrasound assembly 42. The ultrasound assembly 42 comprises wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to a control system 100 via cable 45 (illustrated in FIG. 1). In one arrangement, an electrically insulating potting material 43 fills the inner core 34, surrounding the ultrasound assembly 42, thus preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
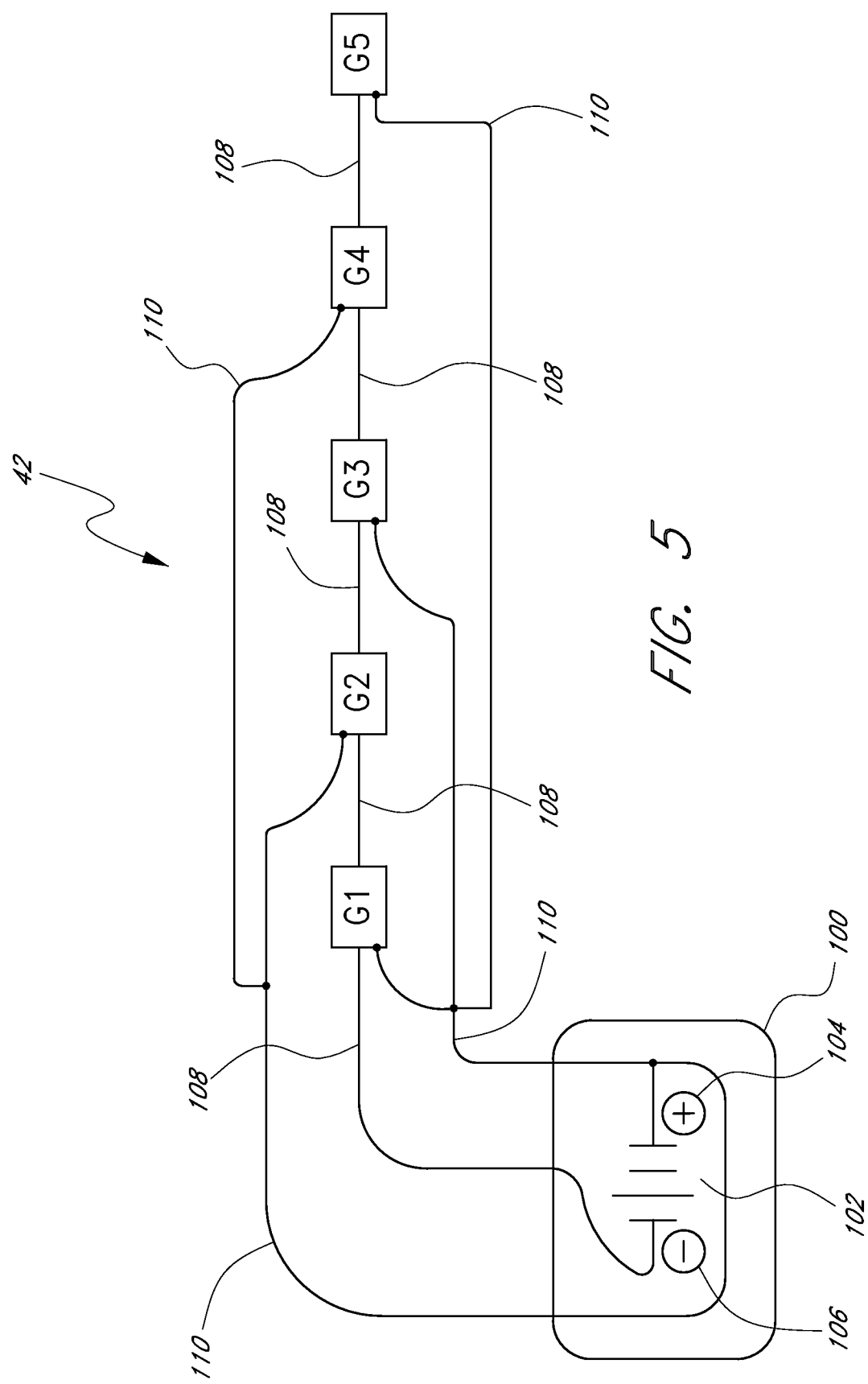
FIG. 5 is a schematic wiring diagram illustrating a technique for electrically connecting five groups of ultrasound radiating members to form an ultrasound assembly.
Figure 6:
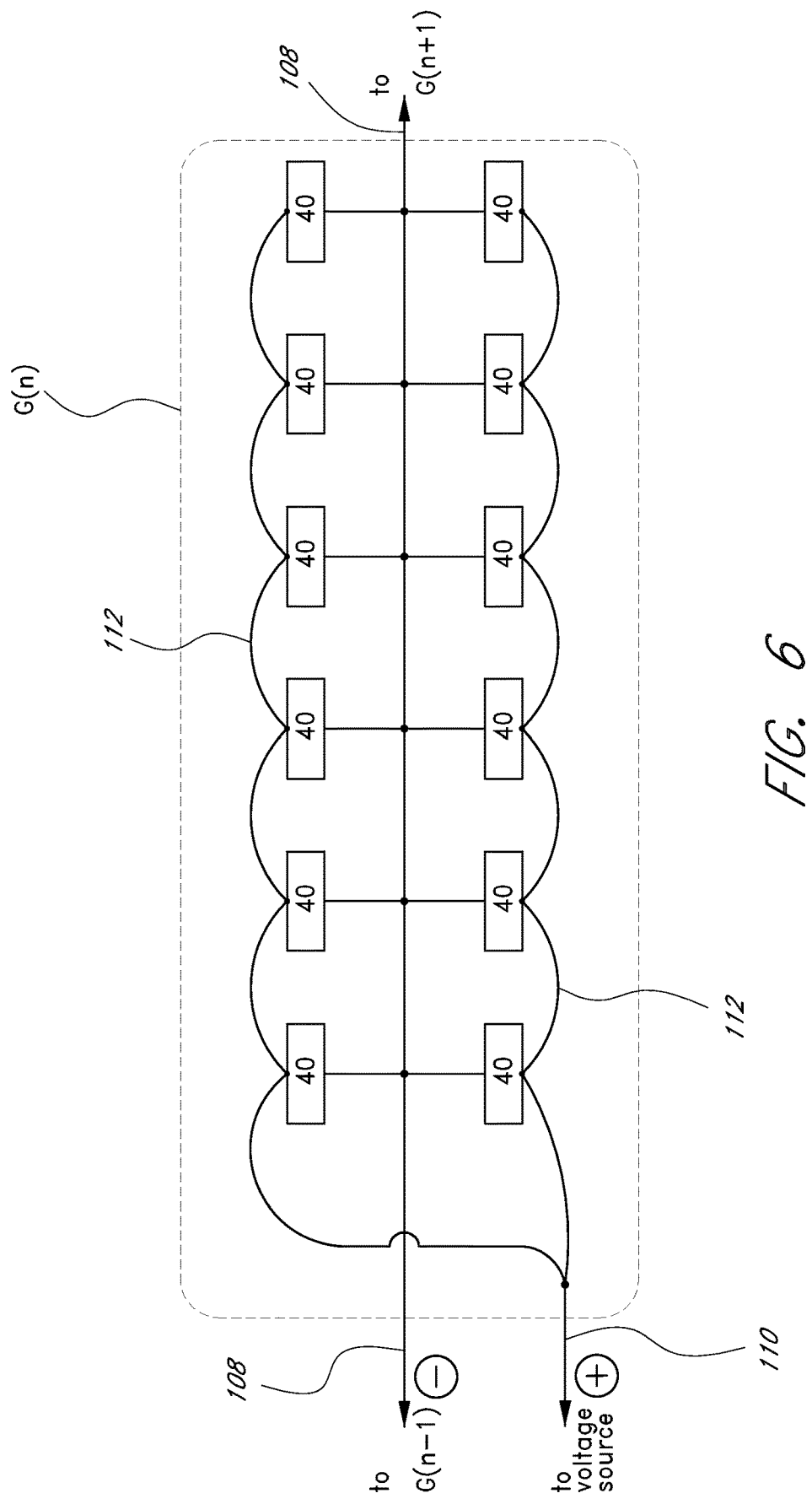
FIG. 6 is a schematic wiring diagram illustrating a technique for electrically connecting one of the groups of FIG. 5.

In some embodiments, the ultrasound assembly 42 comprises a plurality of ultrasound radiating members 40 that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control system 100. In some embodiments, two, three, or four groups of ultrasound radiating member 40 may be electrically connected to each other and the control system 100.

In some embodiments, the ultrasound assembly 42 comprises five or less (i.e., one, two, three, four, or five) ultrasound radiating members 40. The ultrasound radiating members 40 may be divided into one or more groups as described above. The reduced or limited number of ultrasound radiating members 40 can allow the ultrasound assembly 42 to be driven at a higher power.

Still referring to FIG. 5, the control circuitry 100 can include, among other things, a voltage source 102. The voltage source 102 can comprise a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups G1-G5, one of which is illustrated in FIG. 6, is connected to the positive terminal 104 via one of the lead wires 110, and to the negative terminal 106 via the common wire 108. The control circuitry can be configured as part of the control system 100 and can include circuits, control routines, controllers etc configured to vary one or more power parameters used to drive ultrasound radiating members 40, Referring now to FIG. 6, each group G1-G5 comprises a plurality of ultrasound radiating members 40. Each of the ultrasound radiating members 40 is electrically connected to the common wire 108 and to the lead wire 110 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5.

Figure 7A:
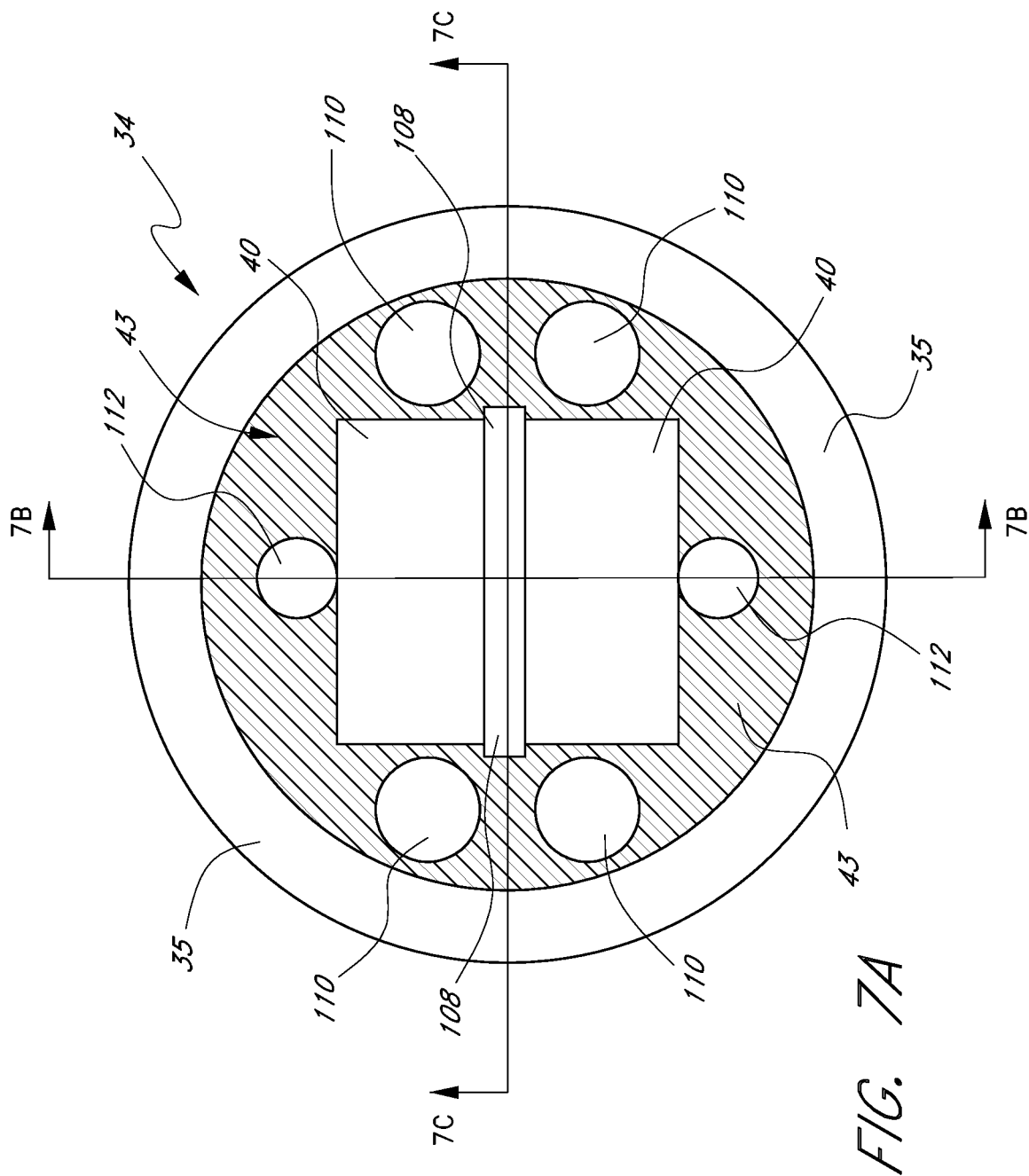
FIG. 7A is a schematic illustration of the ultrasound assembly of FIG. 5 housed within the inner core of FIG. 4.

FIG. 7A illustrates one technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group GI in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

Referring still to FIG. 7A, the common wire 108 comprises an elongate, flat piece of electrically conductive material in electrical contact with a pair of ultrasound radiating members 40. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. Lead wires 110 are can be separated from the other components of the ultrasound assembly 42, thus preventing interference with the operation of the ultrasound radiating members 40 as described above. For example, in one embodiment, the inner core 34 is filled with an insulating potting material 43, thus deterring unwanted electrical contact between the various components of the ultrasound assembly 42.

Figure 7B:
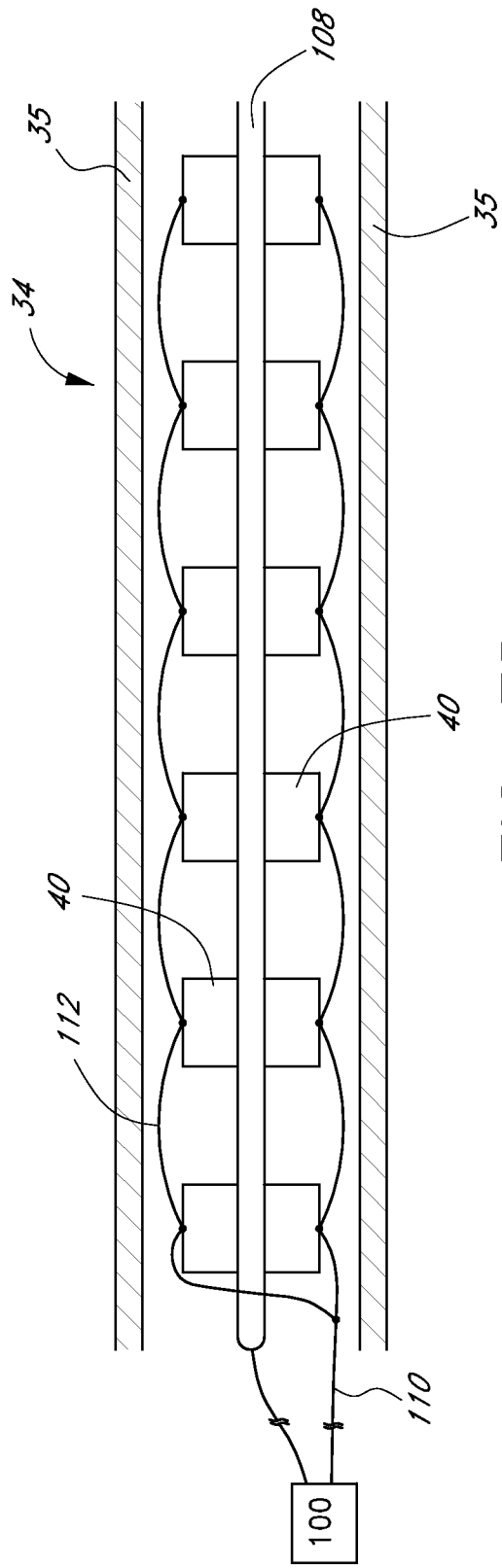
FIG. 7B is a cross-sectional view of the ultrasound assembly of FIG. 7A taken along line 7B-7B.
Figure 7C:
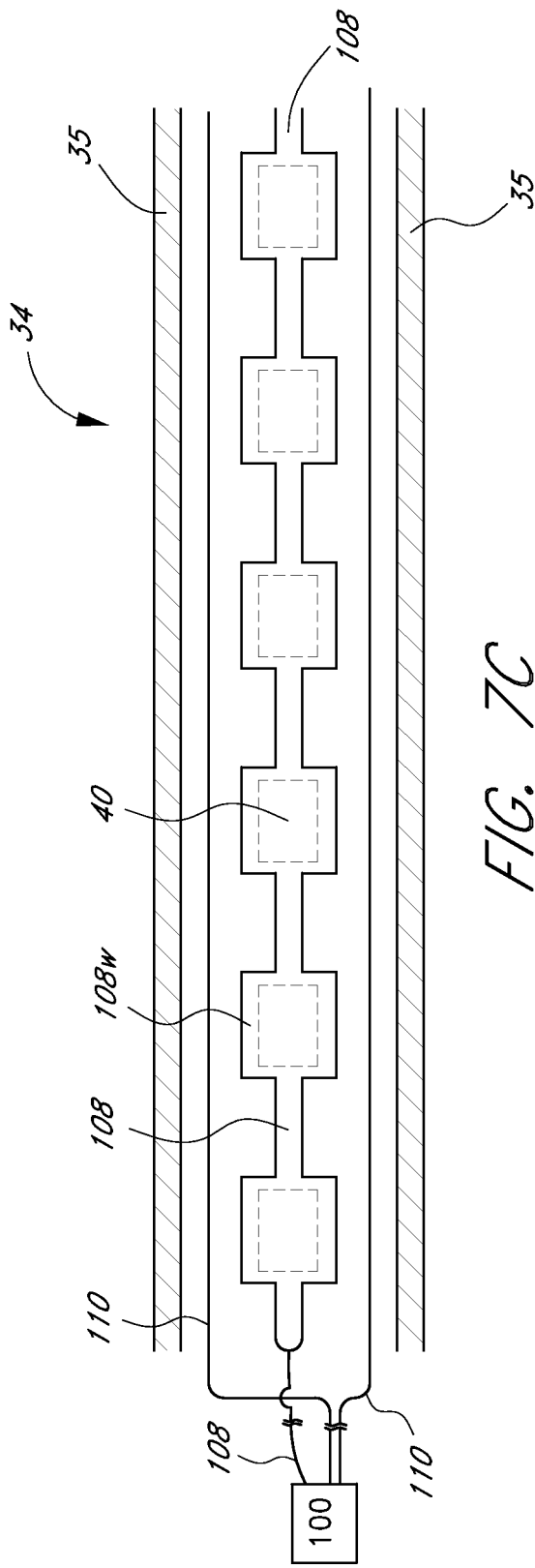
FIG. 7C is a cross-sectional view of the ultrasound assembly of FIG. 7A taken along line 7C-7C.

FIGS. 7B and 7C illustrate cross sectional views of the inner core 34 of FIG. 7A taken along lines 7B-7B and 7C-7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 can include wide regions 108W upon which the ultrasound radiating members 40 can be mounted, thus reducing the likelihood that the paired ultrasound radiating members 40 will short together. In certain embodiments, outside the wide regions 108W, the common wire 108 may have a more conventional, rounded wire shape.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

One of ordinary skill in the art will recognize that the wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the energy delivery section. Such modified embodiments may be advantageous in applications wherein it is desired to deliver a less focused, more diffuse ultrasonic energy field to the treatment site.

In an embodiment, the ultrasound radiating members 40 comprise rectangular lead zirconate titanate ("PZT") ultrasound transducers. In some embodiments, the ultrasound transducer may have dimensions of about 0.017 inches by about 0.010 inches by about 0.080 inches. In other embodiments, other configuration may be used. For example, disc-shaped ultrasound radiating members 40 can be used in other embodiments. In an embodiment, the common wire 108 comprises copper, and is about 0.005 inches thick, although other electrically conductive materials and other dimensions can be used in other embodiments. Lead wires 110 are can comprise 36 gauge electrical conductors, while positive contact wires 112 can be 42 gauge electrical conductors. However, one of ordinary skill in the art will recognize that other wire gauges can be used in other embodiments.

As described above, suitable frequencies for the ultrasound radiating member 40 include, but are not limited to, from about 20 kHz to about 20 MHz. In one embodiment, the frequency is between about 500 kHz and 20 MHz, and in another embodiment 1 MHz and 3 MHz. In some embodiments, the frequency is about 2 MHz to about 3 MHz. In yet another embodiment, the ultrasound radiating members 40 are operated with a frequency of about 2 MHz.

Figure 8:
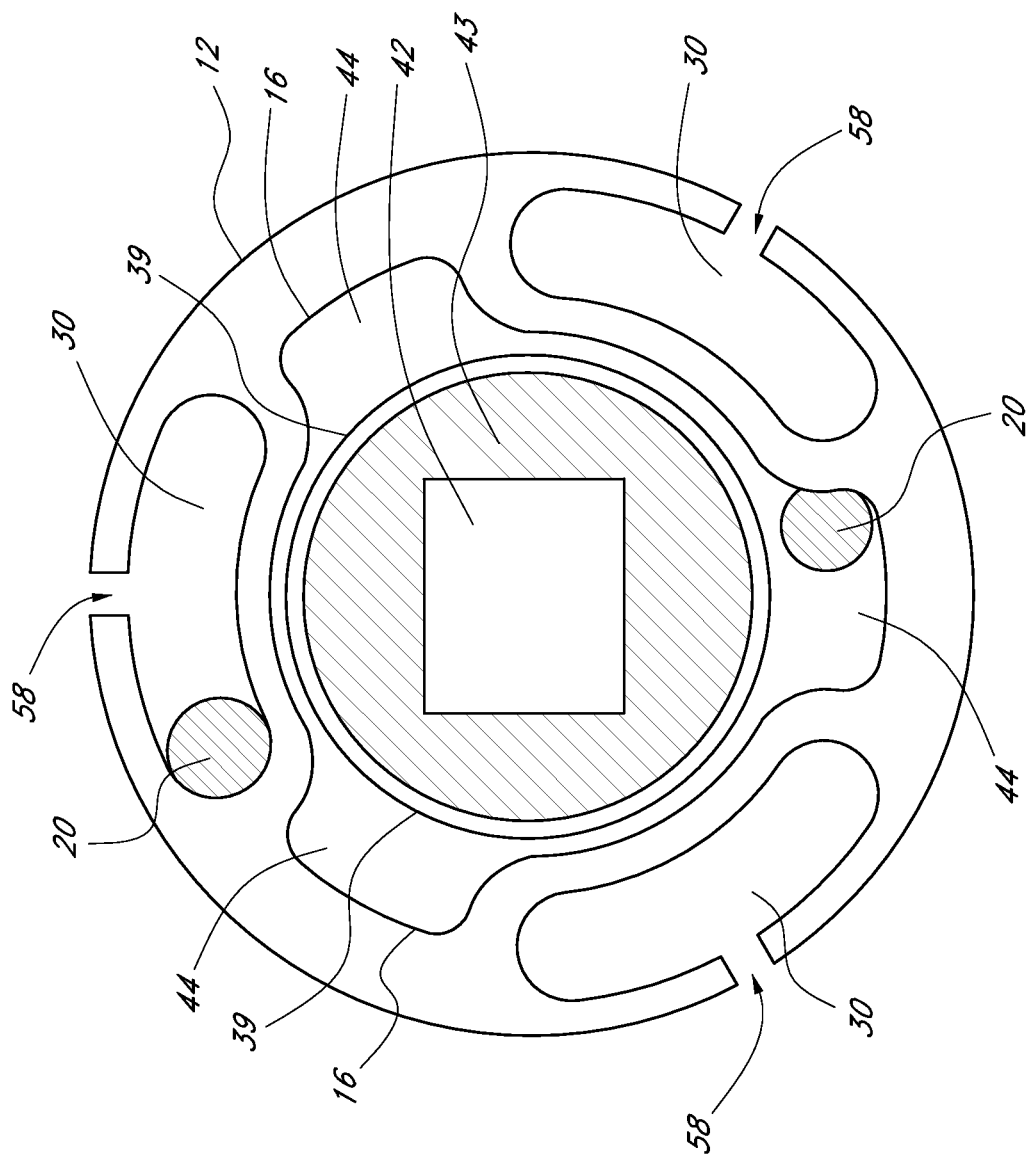
FIG. 8 illustrates the energy delivery section of the inner core of FIG. 4 positioned within the energy delivery section of the tubular body of FIG. 2.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in an embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. Thus, a source of therapeutic compound coupled to the inlet port 32 provides a hydraulic pressure which drives the therapeutic compound through the fluid delivery lumens 30 and out the fluid delivery ports 58.

By evenly spacing the fluid delivery lumens 30 around the circumference of the tubular body 12, as illustrated in FIG. 8, a substantially even flow of therapeutic compound around the circumference of the tubular body 12 can be achieved. In addition, the size, location and geometry of the fluid delivery ports 58 can be selected to provide uniform fluid flow from the fluid delivery ports 30 to the treatment site. For example, in one embodiment, fluid delivery ports closer to the proximal region of the energy delivery section 18 have smaller diameters then fluid delivery closer to the distal region of the energy delivery section 18, thereby allowing uniform delivery of fluid across the entire energy delivery section.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to 0.0020 inches in the distal region of the energy delivery section 18. The increase in size between adjacent fluid delivery ports 58 depends on the material comprising the tubular body 12, and on the size of the fluid delivery lumen 30. The fluid delivery ports 58 can be created in the tubular body 12 by punching, drilling, burning or ablating (such as with a laser), or by any other suitable method. Therapeutic compound flow along the length of the tubular body 12 can also be increased by increasing the density of the fluid delivery ports 58 toward the distal region 15 of the tubular body 12.

It should be appreciated that it may be desirable to provide non-uniform fluid flow from the fluid delivery ports 58 to the treatment site. In such embodiment, the size, location and geometry of the fluid delivery ports 58 can be selected to provide such non-uniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid is introduced through the proximal access port 31 such that cooling fluid flow is produced through cooling fluid lumens 44 and out distal exit port 29 (see FIG. 1). The cooling fluid lumens 44 are can be evenly spaced around the circumference of the tubular body 12 (that is, at approximately 120.degree. increments for a three-lumen configuration), thereby providing uniform cooling fluid flow over the inner core 34. Such a configuration is desirably to remove unwanted thermal energy at the treatment site. As will be explained below, the flow rate of the cooling fluid and the power to the ultrasound assembly 42 can be adjusted to maintain the temp of the inner core energy delivery section 41 within a desired range.

In an embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, the inner core outer body 35 can include a material having the ability to transmit torque. Suitable materials for the inner core outer body 35 include, but are not limited to, polyimides, polyesters, polyurethanes, thermoplastic elastomers and braided polyimides.

In an embodiment, the fluid delivery lumens 30 and the cooling fluid lumens 44 are open at the distal end of the tubular body 12, thereby allowing the therapeutic compound and the cooling fluid to pass into the patient's vasculature at the distal exit port. Or, if desired, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can prevented from passing through the distal exit port by making providing the inner core 34 with a length that is less than the length of the tubular body. In other embodiments, a protrusion is formed on the internal side of the tubular body in the distal region 15, thereby preventing the inner core 34 from passing through the distal exit port.

In still other embodiments, the catheter 10 further comprises an occlusion device (not shown) positioned at the distal exit port 29. The occlusion device can have a reduced inner diameter that can accommodate a guidewire, but that is less than the inner diameter of the central lumen 51. Thus, the inner core 34 is prevented from extending through the occlusion device and out the distal exit port 29. For example, suitable inner diameters for the occlusion device include, but are not limited to, about 0.005 inches to about 0.050 inches. In other embodiments, the occlusion device has a closed end, thus preventing cooling fluid from leaving the catheter 10, and instead recirculating to the proximal region 14 of the tubular body 12. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In certain embodiments, as illustrated in FIG. 8, the tubular body 12 can include one or more temperature sensors 20, which can be located within the energy delivery section 18. In such embodiments, the proximal region 14 of the tubular body 12 includes a temperature sensor lead which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30 (as illustrated), and/or within one or more of the cooling fluid lumens 44.

Figure 9:
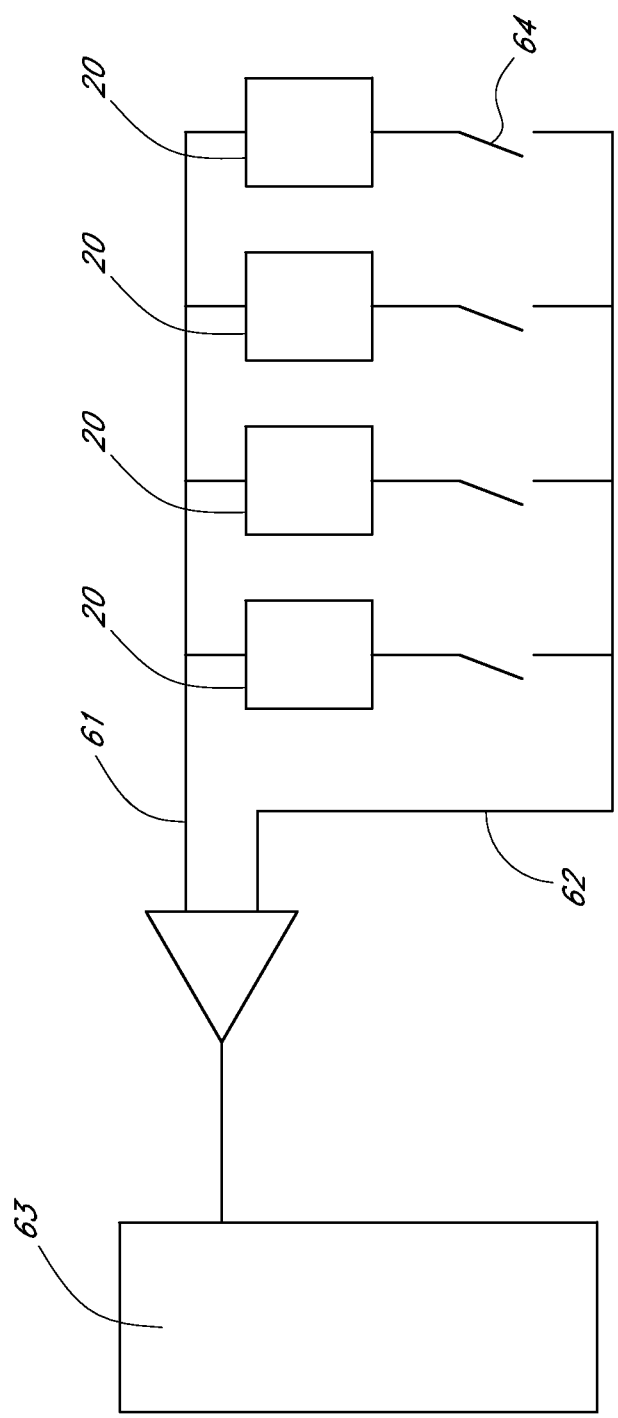
FIG. 9 illustrates a wiring diagram for connecting a plurality of temperature sensors with a common wire.

FIG. 9 illustrates one embodiment for electrically connecting the temperature sensors 20. In such embodiments, each temperature sensor 20 is coupled to a common wire 61 and is associated with an individual return wire 62. Accordingly, n+1 wires can be used to independently sense the temperature at n distinct temperature sensors 20. The temperature at a particular temperature sensor 20 can be determined by closing a switch 64 to complete a circuit between that thermocouple's individual return wire 62 and the common wire 61. In embodiments wherein the temperature sensors 20 comprise thermocouples, the temperature can be calculated from the voltage in the circuit using, for example, a sensing circuit 63, which can be located within the external control circuitry 100.

In other embodiments, each temperature sensor 20 is independently wired. In such embodiments, 2n wires through the tubular body 12 to independently sense the temperature at n independent temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
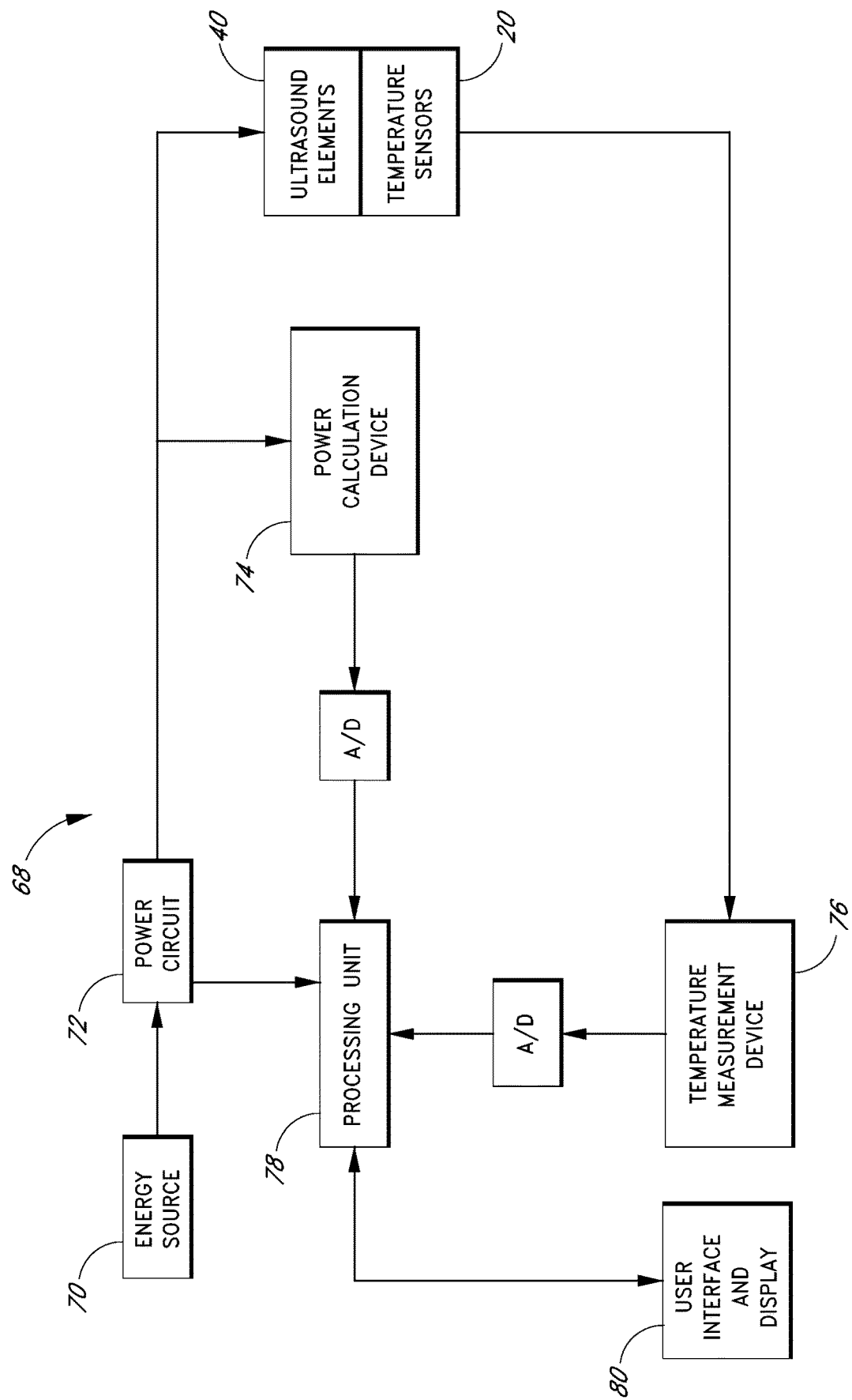
FIG. 10 is a block diagram of a feedback control system for use with an ultrasonic catheter.

FIG. 10 illustrates one embodiment of a feedback control system 68 that can be used with the catheter 10. The feedback control system 68 can be integrated into the control system 100 that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

The feedback control system 68 can include an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In operation, the temperature at each temperature sensor 20 is determined by the temperature measurement device 76. The processing unit 78 receives each determined temperature from the temperature measurement device 76. The determined temperature can then be displayed to the user at the user interface and display 80.

The processing unit 78 comprises logic for generating a temperature control signal. The temperature control signal is proportional to the difference between the measured temperature and a desired temperature. The desired temperature can be determined by the user (at set at the user interface and display 80) or can be preset within the processing unit 78.

The temperature control signal is received by the power circuits 72. The power circuits 72 are can be configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 can be reduced in response to that temperature control signal. Similarly, when the temperature control signal is below a particular level, the power supplied to a particular group of ultrasound radiating members 40 can be increased in response to that temperature control signal. After each power adjustment, the processing unit 78 can monitor the temperature sensors 20 and produces another temperature control signal which is received by the power circuits 72.

The processing unit 78 can further include safety control logic. The safety control logic detects when the temperature at a temperature sensor 20 has exceeded a safety threshold. The processing unit 78 can then provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating member 40 can be identically adjusted in certain embodiments. In a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 also receives a power signal from a power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, it is generally desirable to prevent tissue at a treatment site from increasing more than 6.degree. C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as for example a computer with software. When the processing unit 78 is a computer it can include a central processing unit ("CPU") coupled through a system bus. As is well known in the art, the user interface and display 80 can comprise a mouse, a keyboard, a disk drive, a display monitor, a nonvolatile memory system, or any another. A program memory and a data memory can also be coupled to the bus.

In lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 can then be adjusted according to the preset profiles.

The ultrasound radiating members can be operated in a pulsed mode. For example, in one embodiment, the time average electrical power supplied to the ultrasound radiating members is between about 0.001 watts and about 5 watts and can be between about 0.05 watts and about 3 watts. In certain embodiments, the time average electrical power over treatment time is approximately 0.45 watts or 1.2 watts. The duty cycle is between about 0.01% and about 90% and can be between about 0.1% and about 50%. In certain embodiments, the duty ratio is approximately 7.5%, 15% or a variation between 1% and 30%. The pulse averaged electrical power can be between about 0.01 watts and about 20 watts and can be between approximately 0.1 watts and 20 watts. In certain embodiments, the pulse averaged electrical power is approximately 4 watts, 8 watts, 16 watts, or a variation of 1 to 8 watts. As will be described above, the amplitude, pulse width, pulse repetition frequency, average acoustic pressure or any combination of these parameters can be constant or varied during each pulse or over a set of portions. In a non-linear application of acoustic parameters the above ranges can change significantly. Accordingly, the overall time average electrical power over treatment time may stay the same but not real-time average power.

In one embodiment, the pulse repetition can be between about 1 Hz and about 2 kHz and more can be between about 1 Hz and about 50 Hz. In certain embodiments, the pulse repetition rate is approximately 30 Hz, or a variation of about 10 to about 40 Hz. The pulse duration or width is can be between about 0.5 millisecond and about 50 milliseconds and can be between about 0.1 millisecond and about 25 milliseconds. In certain embodiments, the pulse duration is approximately 2.5 milliseconds, 5 or a variation of 1 to 8 milliseconds. In addition, the average acoustic pressure can be between about 0.1 to about 2 MPa or in another embodiment between about 0.5 or about 0.74 to about 1.7 MPa.

In one particular embodiment, the transducers are operated at an average power of approximately 0.6 watts, a duty cycle of approximately 7.5%, a pulse repetition rate of about 30 Hz, a pulse average electrical power of approximately 8 watts and a pulse duration of approximately 2.5 milliseconds.

The ultrasound radiating member used with the electrical parameters described herein can have an acoustic efficiency greater than about 50% and can be greater than about 75%. The ultrasound radiating member can be formed into a variety of shapes, such as, cylindrical (solid or hollow), flat, bar, triangular, and the like. The length of the ultrasound radiating member can be between about 0.1 cm and about 0.5 cm. The thickness or diameter of the ultrasound radiating members can be between about 0.02 cm and about 0.2 cm.

Figure 11:
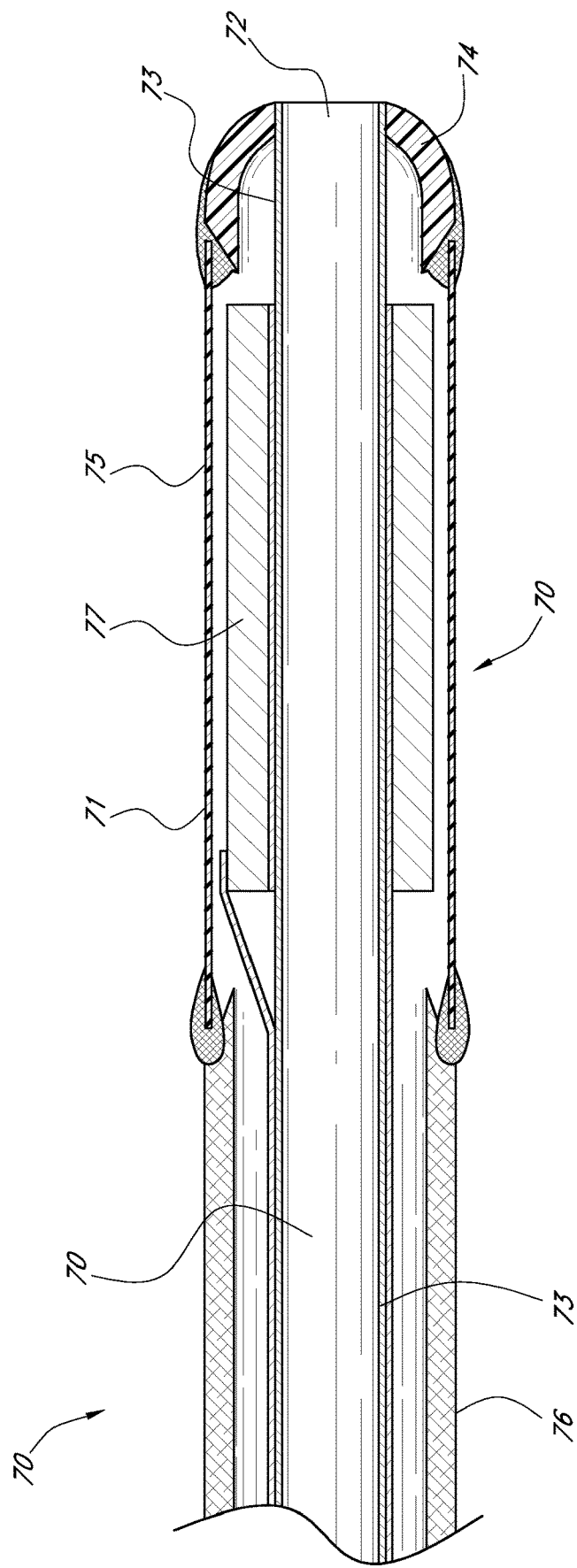
FIG. 11 is a longitudinal cross-sectional view of selected components of an exemplary ultrasound catheter assembly.

With reference now to FIG. 11, a modified embodiment of an energy delivery section 11 of an ultrasound catheter for treating pulmonary embolisms is illustrated. In this embodiment, the catheter can include an inner core 73 that defines a utility lumen 72 configured to pass materials such as a guidewire, a therapeutic compound and/or a cooling fluid. The catheter assembly 70 further includes a distal tip element 74 and a hollow cylindrical ultrasound radiating member 77 that is mounted on the inner core 73. Certain of these components are optional, and are omitted from alternative embodiments. In addition, although only a single ultrasound element is shown, in modified embodiments, more one ultrasound element can be mounted along the lumen 72. For example, in one embodiment, three ultrasound elements are mounted longitudinally next to each other along the inner core 73. In other embodiments, the ultrasound elements can be rectangular, discs or other shapes. For example, in one arrangement, the cylindrical element can be replaced with a plurality of smaller elements positioned radially about the inner core 73. As with the embodiments described above, the catheter 11 of FIG. 11 is configured to be introduced into the major blood vessels leading from the heart to the lungs (e.g., the pulmonary artery). In one embodiment of use, femoral venous access may be used to place the catheter 11 into such vessels. In such embodiments, the catheter 11 can be advanced through femoral access site, through the heart and into the pulmonary artery. The dimensions of the catheter 11 are adjusted based on the particular application for which the catheter 11 is to be used.

As noted above, the PZT transducer which forms the ultrasound elements described above can be by specific electrical parameters (herein "power parameters" or "acoustic parameters" that cause it to vibrate in a way that generates ultrasonic energy). In certain embodiments, the "power parameters" or "acoustic parameters" can be non-linearly varying or modulating (e.g., randomly or pseudo randomly) one or more of the power parameters or acoustic parameters, the effectiveness of the ultrasound catheter (e.g., the effectiveness of enhancing the removal of a thrombus) can be significantly enhanced. By non-linearly varying or modulating one or more of the acoustic parameters, the ultrasound radiating members create nonlinear acoustic pressure, which as described above can increase the effectiveness of the acoustic pressure in enhancing the delivery of a therapeutic compound. Examples of nonlinear variances or modulation include, but are not limited to, multi variable variations, variations as a function of a complex equation, sinusoidal variations, exponential variations, random variations, pseudo random variations and/or arbitrary variations. In other arrangements it is anticipate that one or more of the parameters discussed can be varied in a linear manner either alone or combination with the nonlinear variance.

Figure 12:
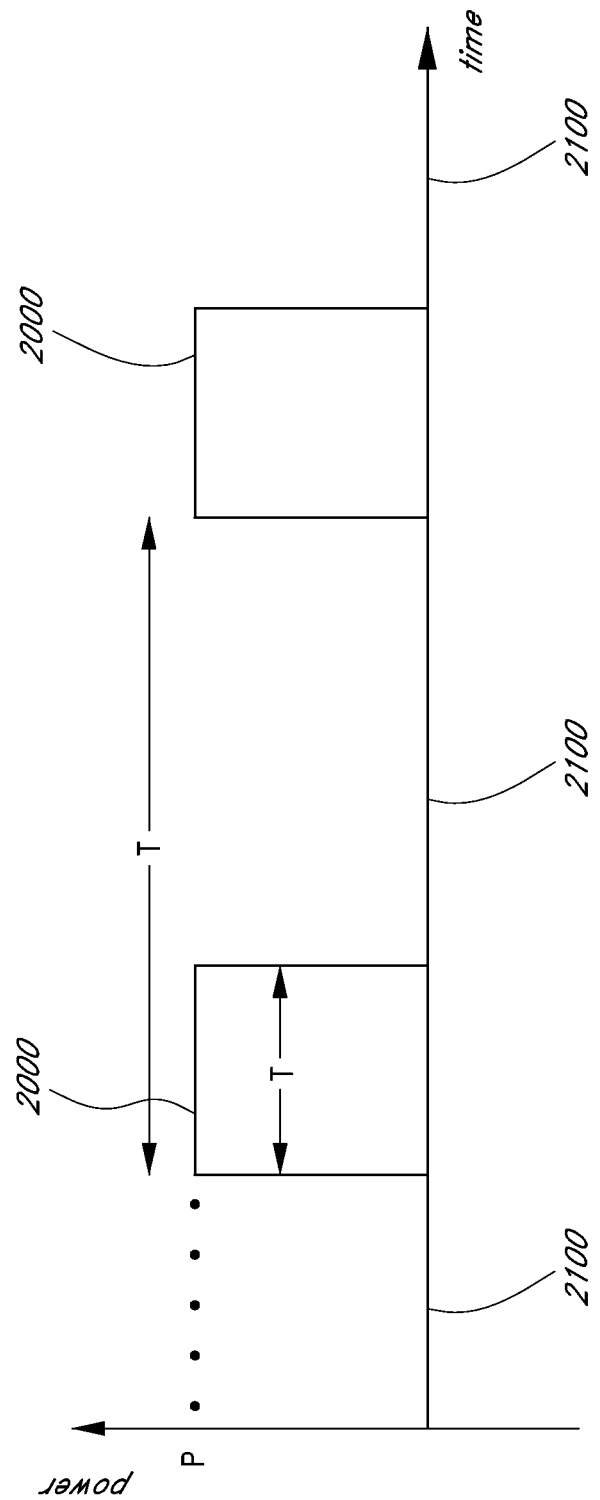
FIG. 12 schematically illustrates an example ultrasonic energy pulse profile.

FIG. 12 will be used to explain certain power parameters which can used to drive the ultrasound radiating members. As shown, the members can be driven a series of pulses 2000 having peak power P or amplitude and duration τ. During these pulses 2000, the ultrasound radiating members as driven at a certain frequency f as described above by the electrical current. The pulses 2000 can be separated by "off" periods 2100. The cycle period T is defined as the time between pulse initiations, and thus the pulse repetition frequency ("PRF") is given by $T^{-1}$. The duty cycle is defined as the ratio of time of one pulse to the time between pulse initiations $\tau T^{-1}$, and represents the fraction of time that ultrasonic energy is being delivered to the treatment site. The average power delivered in each cycle period is given by $P\tau T^{-1}$. Accordingly, the illustrated embodiment, the ultrasound radiating members are operated using pulses, or modulated electrical drive power instead of continuous drive power In one embodiment, the average power delivered in each cycle period can be between about 0.1 watts and about 2.0 watts. In such an embodiment, each cycle period has a different average power value, wherein the average power values for the different cycles vary in a nonlinear fashion. Examples of non-linear variation include, but are not limited to, simple or complex variable or multi-variable equations, varying randomly, pseudo randomly and/or in an arbitrary manner. For instance, in one such modified embodiment, each cycle period has an average power quantity that is randomly or pseudo randomly distributed between a maximum average power quantity and a minimum average power quantity. The average power of each cycle period can be adjusted by manipulating one or more parameters of the waveform in the cycle period, such as, but not limited to, peak power P, reduced power P', pulse repetition frequency, pulse duration $\tau$, and duty cycle.

In another embodiment, the duty cycle is can be between about 1% and about 50%, can be between about 2% and about 28%. During operation of the catheter, the duty cycle can vary in a nonlinear fashion. For instance, in one such modified embodiment, the duty cycle that is randomly or pseudo randomly distributed between a maximum duty cycle and a minimum duty cycle. For example, in one embodiment, the values for the maximum duty cycle are between about 25% and about 30%, and typical values for the minimum duty cycle are between about 1.5% and about 3.5%. In yet another embodiment, the duty cycle is varied non-linearly from a minimum value of about 2.3% and a maximum value of about 27.3%. In one embodiment, other parameters of the waveform are manipulated such that each cycle period has the same average power, even though the duty cycle for each cycle period is varying in a nonlinear fashion.

In another embodiment, the peak power P delivered to the treatment site can be between about 0.1 watts and about 20 watts, can be between about 5 watts and about 20 watts, and can be between about 8 watts and about 16 watts. Within the ranges, during operation of the catheter, the peak power P can vary in a nonlinear fashion. For instance, in one such modified embodiment, each cycle period has a peak power quantity that is randomly or pseudo randomly distributed between a maximum peak power $P_{max}$ and a minimum peak power $P_{min}$. Typical values for the maximum peak power $P_{max}$ are between about 6.8 watts and about 8.8 watts, and typical values for the minimum peak power $P_{min}$ are between about 0.1 watts and about 1.0 watts. In another embodiment, the peak power is varied non-linearly between a maximum peak power $P_{max}$ of about 7.8 watts and a minimum peak power $P_{min}$ of about 0.5 watts. In one embodiment, other parameters of the waveform are manipulated such that each cycle period has the same average power, even though the peak power P for each cycle period is varying in a nonlinear fashion.

In another embodiment, the effect of a therapeutic compound is optionally enhanced by using a certain pulse repetition frequency PRF and/or a certain pulse duration $\tau$. In one example embodiment, the PRF can be between about 5 Hz and about 150 Hz, can be between about 10 Hz and about 50 Hz, and can be between about 20 Hz and about 40 Hz. In one embodiment, the PRF remains substantially constant during the course of a treatment. However, in certain modified embodiments the PRF is non-linearly varied during the course of a treatment within the ranges described above. For example, in one such modified embodiment the PRF is varied linearly during the course of the treatment, while in another such modified embodiment the PRF is varied nonlinearly during the course of the treatment. Examples of nonlinear variances include, but are not limited to, sinusoidal variations, exponential variations, and random variations. For instance, in an example embodiment the PRF is varied randomly between a maximum PRF and a minimum PRF during the course of a treatment. Typical values for the maximum PRF are between about 28 Hz and about 48 Hz, and typical values for the minimum PRF are between about 5 Hz and about 15 Hz. In another embodiment, the maximum PRF is about 38 Hz and the minimum is about 10 Hz. In one embodiment, the pulse repetition interval is varied between about 25 to about 100 ms.

The pulse amplitude, pulse width and pulse repetition frequency during each pulse can also be constant or varied in a non-linear fashion as described herein. Other parameters are used in other embodiments depending on the particular application.

In one example embodiment, the pulse duration $\tau$ can be between about 1 millisecond and about 50 milliseconds, can be between about 1 millisecond and about 25 milliseconds, and can be between about 2.5 milliseconds and about 5 milliseconds. In a modified embodiment, each cycle period has a different pulse duration $\tau$, wherein the pulse duration values vary in a nonlinear fashion with the ranges described above. For instance, in one such modified embodiment, each cycle period has a pulse duration quantity that is randomly distributed between a maximum pulse duration $\tau_{max}$ and a minimum pulse duration $\tau_{min}$. Typical values for the maximum pulse duration $\tau_{max}$ are between about 6 milliseconds and about 10 milliseconds (and in one embodiment about 8 milliseconds), and typical values for the minimum pulse duration $\tau_{min}$ are between about 0.1 milliseconds and about 2.0 milliseconds (and in one embodiment 1 millisecond), In one embodiment, other parameters of the waveform are manipulated such that each cycle period has the same average power, even though the pulse duration $\tau$ for each cycle period is varying in a nonlinear fashion. In other embodiments, the average power can be varied non-linearly.

In addition, the average acoustic pressure can also non-linearly varied as described above between about 0.1 to about 2 MPa or in another embodiment between about 0.5 or about 0.74 to about 1.7 MPa.

The control system 100 can be configured to vary one or more of the power parameters as discussed above. Accordingly, the control system 100 can include any of a variety of control routines, control circuits, etc. so as to vary the power parameters described above. As mentioned above, the control parameters can be varied in combination with other operating parameters (e.g., frequency) of the ultrasound radiating member and/or catheter. Alternatively, the power parameters may be varied using a software package that controls the operation of the ultrasound radiating members. It should also be appreciated that one, two, three or all of the parameters (and subsets thereof) can be non-linearly varied at the same time or by themselves.

In other embodiments, the power or acoustic parameters can be kept constant or substantially constant during operation of the ultrasound system.

In one embodiment, one way of implementing a randomization protocol is to generate and execute a plurality of ultrasonic cycle profiles, where each ultrasonic cycle profile can have randomly generated power parameter values. As previously mentioned, power parameters include, but are not limited to, peak power, pulse width, pulse repetition frequency and pulse repetition interval. Generally, for each power parameter, a random number generator, for example, can be used to select a value within a bounded range determined by the operator. Examples of suitable ranges are described above. For example, one ultrasonic cycle profile can have a randomly selected peak power value, while the other power parameters are non-randomly selected. Another ultrasonic cycle profile may have a plurality of randomly selected power parameters values, such as peak power and pulse width. This process can be used to generate the desired number of ultrasonic cycle profiles.

Each ultrasonic cycle profile can be run for a profile execution time. For example, if the profile execution time is approximately 5 seconds, each ultrasonic cycle profile will be run for approximately 5 seconds before the next ultrasonic cycle profile is run. In some embodiments, the profile execution time is less than about 5 seconds. For example, in some embodiments the profile execution time is between about one second and about 30 seconds. In some embodiments, the profile execution time is less than about one second. In some embodiments, the profile execution time is increased so that accurate measurements can be taken of the executed power parameters. In some embodiments, the profile execution time itself can be selected randomly from a predetermined range.

In some embodiments, it is desirable to deliver a particular time averaged power. Because the power parameters may be randomized, it may take the execution of a plurality of ultrasonic cycle profiles before the time averaged power approaches an asymptotic value. In some embodiments, the execution of about 40 to about 50 ultrasonic cycle profiles is required for the time averaged power to become asymptotic. In other embodiments, less than about 40 ultrasonic cycle profiles are required, while in yet other embodiments, more than about 50 ultrasonic cycle profiles are required. In some embodiments, ultrasonic cycle profiles are executed until the time average power approaches an asymptotic value. For example, if the profile execution time is 5 seconds and the overall execution time is 30 minutes, 360 ultrasonic cycle profiles will be executed, which in some embodiments is sufficient for the time average power to approach an asymptotic value.

Many of the above-described parameters relate to the electrical input parameters of the ultrasonic elements of the catheter. Varying these electrical parameters results in varying the acoustic output of the catheter. Accordingly, the desired affect of non-linearly or randomly varying or modulating the acoustic parameters can also be described directly.

Figure 13:
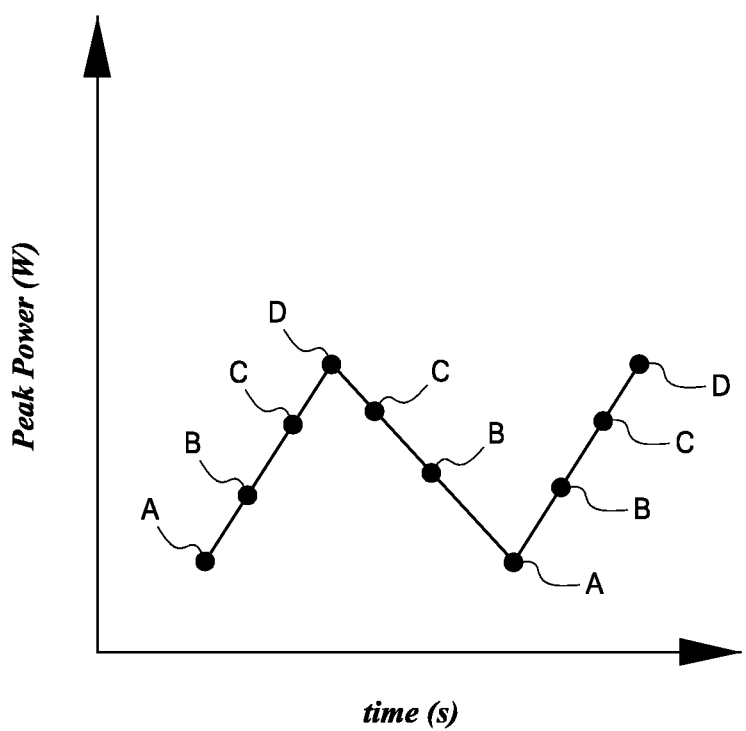
FIG. 13 is a chart illustrating Peak Power (W) as a function of time according to one embodiment.

FIG. 13 illustrates an embodiment in which peak power or peak acoustic pressure is varied in specific manner. Specifically, in this embodiment, peak power or peak acoustic pressure is repeatedly increased and decreased over time. As shown, the peak power can be increased and then decreased (e.g., ramped up to a peak value than ramped down to a minimum value) in a linear manner. However, in modified embodiments, the peak power or peak acoustic pressure can be increased to a specific value and then decreased to a specific value in a non-linear or pseudo-random manner (e.g., a sinusoidal, curved, or non-linear or complex profile). In the illustrated embodiment, the peak power is ramped up and down by moving through discrete peak power values labeled A-D. However, more or less values can be used or a substantially continuous ramping can also be used. In some embodiments, the maximum and minimum peak values between which the peak power or peak acoustic pressure is ramped, can be changed and/or varied over time. In some embodiments, the each of the maximum and the minimum values remains constant. In some embodiments, the peak power or peak acoustic pressure can also be ramped repeatedly between a second minimum value and a second maximum value.

In one embodiment, the peak power varies from about 0.1 Watts to about 30 Watts and in another embodiment from about 1.5 Watts to about 8 Watts. Within these ranges, in one embodiment, the peak power can have between about 1 to 5 discrete values and in another embodiment 2 specific values.

In some embodiments, while the peak power or peak acoustic pressure is ramped up and down, the other power parameters can remain constant, substantially constant and/or varied (e.g., as described above). For example, Table 2 shows the power parameters for one embodiment in which peak powers ramped between about 1.5 and about 7.88 W. During this ramping, pulse width (PW) and pulse repetition frequency (PRF) are varied. In this embodiment, pulse width and pulse repetition frequency were varied in a manner to maintain pulse repetition (PRF) is 20-40 Hz, in other embodiments the pulse repetition can be maintained within 15-45 Hz. In one embodiment, the pulse length (pulse width, PW) can be adjusted to each selected pulse repetition frequency to ensure that temporal average power over treatment time and resulting thermal index (heat generation) remains within a clinically acceptable range.

TABLE 2

Example Power Protocol

| PeakPower (W) | PW (mSec) | PRF (Hz) |
|---|---|---|
| 5 | 6.86 | 26 |
| 2.5 | 5 | 24 |
| 1.5 | 8.06 | 21 |
| 2.5 | 5 | 27 |
| 5 | 6.86 | 21 |
| 7.88 | 4 | 24 |
| 5 | 6.86 | 26 |
| 2.5 | 5 | 24 |
| 1.5 | 8.06 | 21 |
| 2.5 | 5 | 27 |
| 5 | 6.86 | 21 |
| 7.88 | 4 | 24 |

Similarly, the physiological parameter described above can also be varied in the same manner as varying the peak power. In some embodiments, the physiological parameter can be ramped up- and down-wards between a minimum value and a maximum value. The maximum and the minimum values may not be the same as the maximum and the minimum values for the peak power ramping. In some embodiments, the ramping of the physiological parameter may also be done in a linear manner, and in other embodiments, the ramping can be done in a non-linear or pseudo-linear manner (e.g., a sinusoidal, curved, or non-linear or complex profile). As with the peak power, the physiological parameter can be ramped up and down by moving through discrete physiological parameter values. In some embodiments, the maximum and minimum values between which the physiological parameter is ramped can be changed and/or varied over time. In some embodiments, each of the maximum and the minimum values remains constant.

In some embodiments, both the peak power and at least one physiological parameter can be varied in any of the manner described above at the same time. For example, both the peak power and the physiological parameter may be ramped up and down in a linear manner or in a non-linear or pseudo-linear manner at the same time. However, in some embodiments, the peak power may be ramped in a non-linear manner while the physiological parameter is ramped in a linear manner. In other embodiments, the peak power may be ramped in a linear manner while the physiological parameter is ramped in a non-linear manner.

Varying peak power and/or physiological parameter as described above has particular advantages. For example, Applicants believe that ramping peak power and/or physiological parameter creates acoustic "momentum" that advantageously results in radiation force transfer to media such as effectively accelerating acoustic streaming, which can enhance the therapeutic effects (described above) of the ultrasound.

Pulmonary Embolism Treatment

As noted above, the ultrasound catheters 10, 11 can also be used for treating PE. The ultrasound catheters 10, 11 can introduced into a patient's pulmonary artery over a guidewire. The distal portion 15 of the ultrasound catheter 10 is then advanced to the treatment site within the pulmonary artery. The ultrasound energy delivery section 18 of the ultrasound catheter can be positioned across the treatment site using fluoroscopic guidance via radiopaque marker located near the proximal end and the distal end of the ultrasound energy delivery section 18. Once the ultrasound catheter 10 is successfully placed, the guidewire may be removed from the ultrasound catheter 10.

In the embodiments depicted in FIGS. 2-10, the elongate inner core 34 comprising at least one ultrasound radiating member 40 can then be inserted into the central lumen 51 of the ultrasound catheter 10. The at least one ultrasound radiating member 40 can positioned along the energy delivery section 18 of the ultrasound catheter 10. In some embodiments, at least one cooling lumen 44 is formed between an outer surface 39 of the inner core 34 and an inner surface 16 of the tubular body 12. The coolant infusion pump is attached to the cooling fluid fitting 46, which is in communication with the at least one cooling lumen 44. The drug infusion pump can then be connected to the therapeutic compound inlet port 32, which is in communication with the at least one fluid delivery lumen 30.

The thrombolytic drug can then be delivered to the treatment site through at least one fluid delivery lumen 30. In some embodiments, a plurality of fluid delivery ports 58 in fluid communication with the fluid delivery lumen 30 can be located on the ultrasound catheter at the ultrasound energy delivery section 18. The drug can be infused through the fluid delivery ports 58 to the treatment site.

When the ultrasound catheter such as the embodiment depicted in FIG. 11 is used, the thrombolytic drug is delivered to the treatment site through the utility lumen 72 and out of the distal exit port 29. In some embodiments, the drug can be delivered through the utility lumen 72 with the guide wire still positioned within the utility lumen 72.

The ultrasound energy may be delivered to the treatment site simultaneously or intermittently with the infusion of the thrombolytic drug. In some embodiments, the ultrasound energy is emitted to the treatment site prior to the thrombolytic drug being delivered. In some embodiments, the thrombolytic drug is delivered to the treatment site prior to the ultrasound energy being emitted. The ultrasound energy may be emitted according to the manner described above. In some embodiment, the power parameter and the physiological parameter of at least one ultrasound radiating member 40 may be varied as described above.

In some embodiments, the elongate inner core 34 may comprise five or less (i.e., one, two, three, four, or five) ultrasound radiating members 40. In some embodiments, the ultrasound catheter depicted in FIG. 11 may have five or less (i.e., one, two, three, four, or five) hollow cylindrical ultrasound radiating members 77. By limiting the number of the ultrasound radiating members 40 or 77, it is can be possible to drive the ultrasound radiating members at a higher power for PE treatments.

High intensity ultrasound catheter may also be especially effective in treating pulmonary embolism. In some embodiments, the size of one or more ultrasound radiating members 40 positioned in the elongate inner core 34 and one or more hollow cylindrical ultrasound radiation members 77 can be increased to generate high intensity ultrasound. In other words, larger ultrasound radiating members can be used for this purpose. In some embodiments, positioning the ultrasound radiating members less than 1 cm apart can also result in higher intensity ultrasound output.

Without being bound to the theory, the ultrasound can prepare the clot by unwinding the fibrin strands and increasing the permeability of the clot. Acoustic pressure waves and micro-streaming force the delivered drug into the clot, quickly permeating the clot with drug. As the drug is absorbed into the clot it binds with exposed plasminogen receptor sites. Once bound in the clot, the drug is no longer in free circulation, does not pass through the liver and is not metabolized.

In some embodiments, recombinant tissue plasminogen activator (rt-PA or Actilyse®) can be used with the ultrasound catheter 10 for the treatment of pulmonary embolism. The effective infusion dosage may range from about 0.12 mg/hr to about 2 mg/hr, from about 0.2 mg/hr to about 1.5 mg/hr, from about 0.5 mg/hr to about 1.5 mg/hr, or from about 1 mg/hr to about 2 mg/hr. The rt-PA maximum total infusion dose may be from about 10 mg to about 30 mg, from about 10 mg to about 20 mg, or about 25 mg. In some embodiment, as rt-PA is infused at a rate of about 1 mg/hr to about 2 mg/hr for about 3 to about 5 hours, then the infusion rate is decreased to about 0.5 mg/hr for 10 hours. In some embodiments, rt-PA is infused at a rate of about 1 mg/hr to about 2 mg/hr for about 5 hours, then the infusion rate is decreased to about 0.5 mg/hr for 10 hours.

Other potential drugs that may be used with the ultrasound catheter for treating pulmonary embolism may include fibrinolytic compounds such as urokinase (Abbokinase®, Abbott laboratories, USA), streptokinase (Streptase®, Behringwerke AG), and reteplase (Retavase™, Centocor, Inc.). The enzymatic activity and stability of these fibrinolytics (including rt-PA) are not changed after exposure to therapeutic ultrasound.

In general, digital angiographic equipment is used to aid the performance of the ultrasound catheter treatment procedure. Continuous invasive pressure monitoring and ECG-monitoring can be used for obtaining baseline hemodynamic parameters, including heart rate, right atrial, right ventricular, and pulmonary artery pressures, as well as the mixed-venous oxygen saturation from the pulmonary artery. A systemic arterial blood pressure and a systemic oxygen saturation can also be measured if an arterial line is in place. Otherwise, the systemic cuff blood pressure is measured and the oxygen saturation is obtained by pulse oximetry. In one embodiment, a blood pressure sensor is integrated into the ultrasound catheter.

In some embodiments, a feedback control loop configured to monitor the baseline hemodynamic parameters and/or mixed-venous oxygen saturation can be integrated into the control system 100. The output power of the energy source can then be adjusted according to the readings. A physician can override the closed or open loop system if so desired.

In some embodiments, an unilateral filling defect in one main or proximal lower lobe pulmonary artery by contrast-enhanced chest CT indicates that only one ultrasound catheter is to be placed into the pulmonary artery. In case of bilateral filling defect is detected in both main or proximal lower lobe pulmonary arteries by contrast-enhancing chest CT, two ultrasound catheters may be placed.

Figure 14:
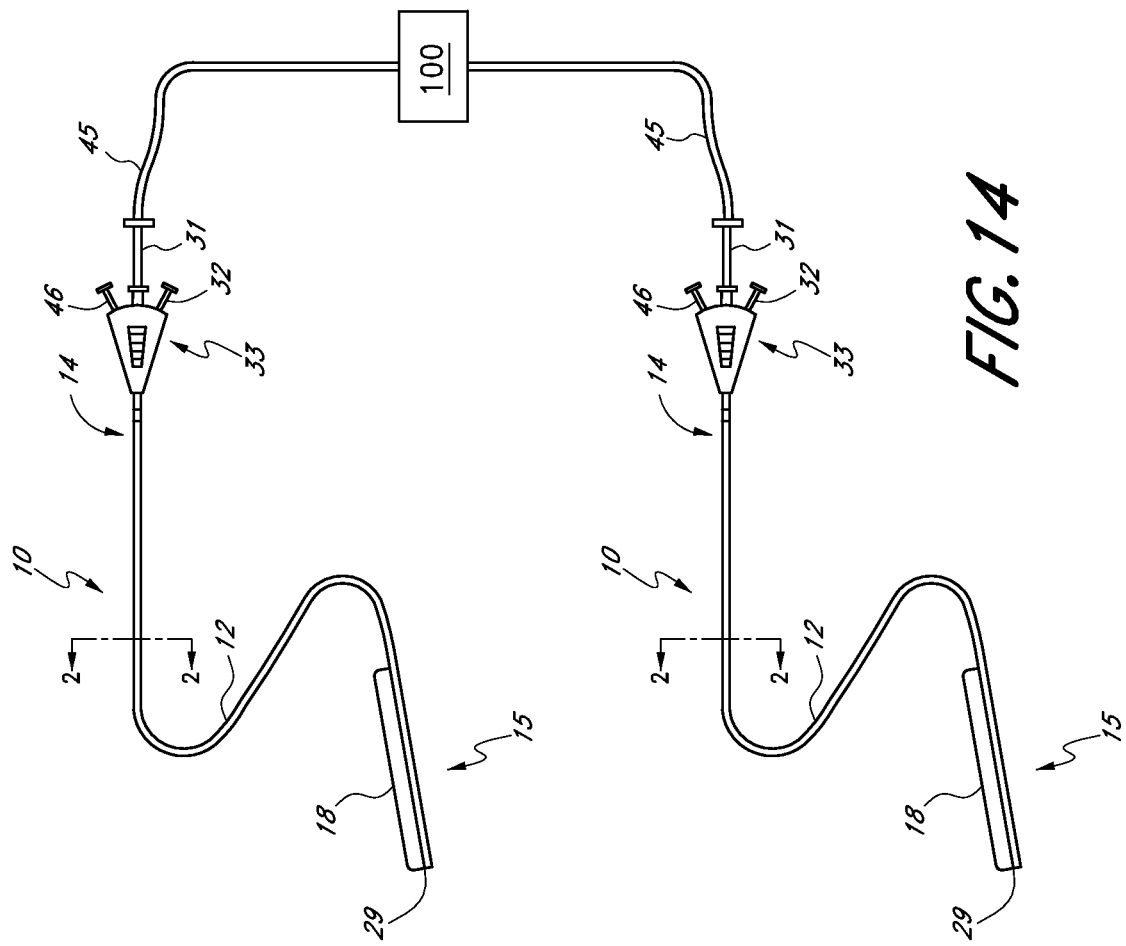
FIG. 14 illustrates an pair of ultrasound catheters operatively connected to a common control system.
Figure 15:
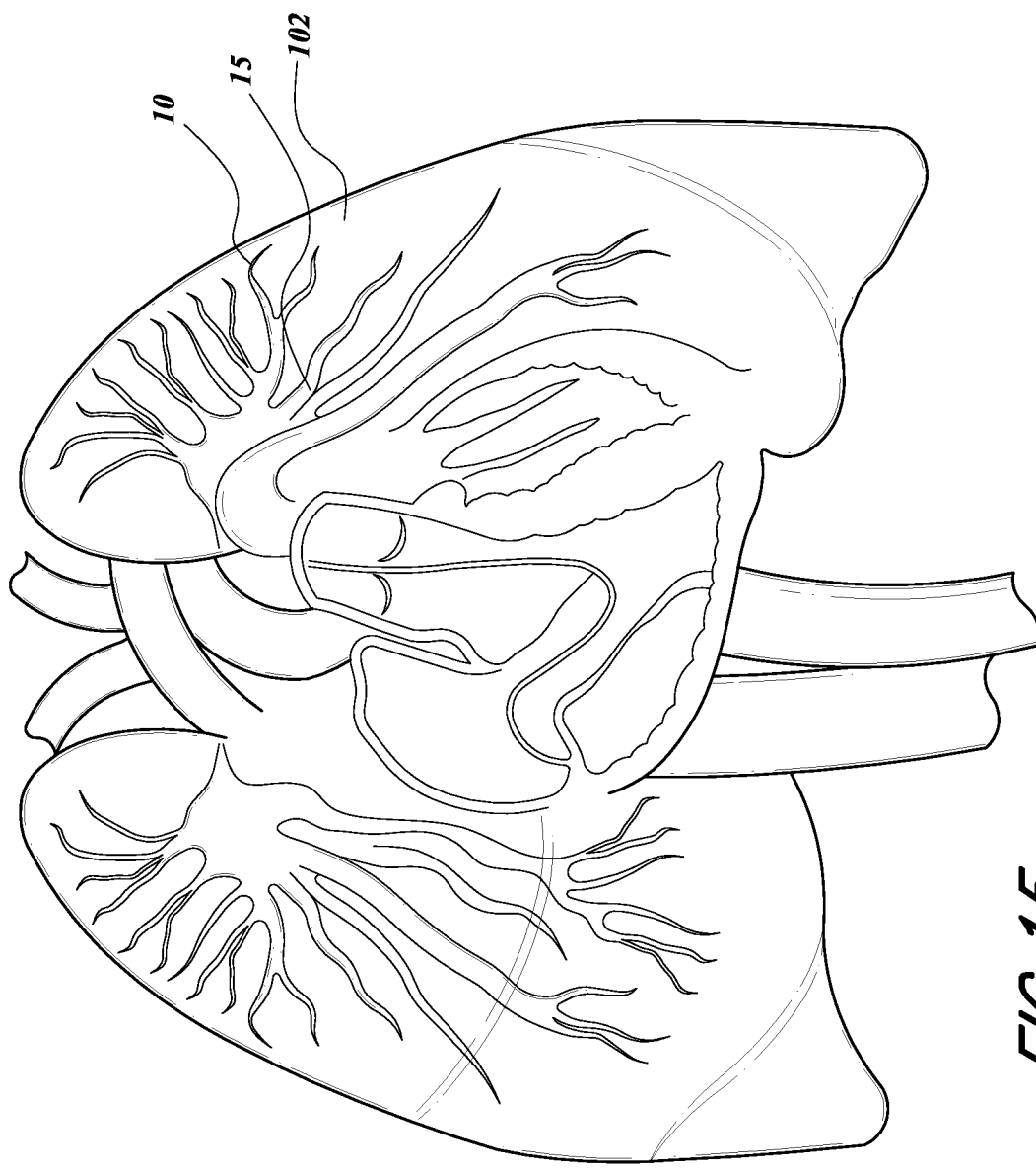
FIG. 15 illustrates an ultrasound catheter positioned within a pulmonary artery.

In some embodiments where two ultrasound catheters are placed for treating bilateral filling defect, the two catheters may be controlled by a single control unit 100 as illustrated in FIG. 14. Each ultrasound catheter 10 (or for example the catheter of FIG. 11) can connected to the single control unit 100 via a cable 45. The control system 100 can control each ultrasound catheter 10 as described above. FIG. 15 illustrates the one catheter positioned within one pulmonary artery. In a bilateral application, the second catheter can be inserted along side the first catheter diverging at the bifurcation of pulmonary trunk into right and left pulmonary arteries.

The control unit 100 may be configured to control two catheters separately, or may be configured to control two catheters simultaneously. In some embodiments, the control system 100 can be configured to vary one or more of the power parameters of each ultrasound catheter independently. The control system 100 can also be configured to vary the power parameters the same way on both ultrasound catheters. In this case, the two ultrasound catheters can be operated or controlled as one unit.

The power to each ultrasound catheter can also be shut off independently should the temperature of one of the treatment sites or the particular ultrasound element becomes too high, or if the clot in one pulmonary artery has been dissolved or reduced before the other. The ability to turn off the particular ultrasound catheter independently can limit the potential damage to the treatment site or the ultrasound catheter.

In some embodiments, the initial rt-PA infusion rate for unilateral filling defect would be about 1 mg/hr (one ultrasound catheter), while the initial infusion rate for bilateral filling defect would be about 2 mg/hr (two ultrasound catheters).

As noted above, in some embodiments, femoral venous access may be used for placing the ultrasound catheter in the pulmonary arteries. For example, a 6 F introducer sheath is inserted in the common femoral vein. An exchange-length 0.035-inch angled guidewire, for example the Terumo® soft wire, may be used for probing the embolic occlusion under fluoroscopy. A 5 F standard angiographic catheter, such as a multipurpose catheter or pigtail catheter or any other pulmonary angiographic catheter may be used with small manual contrast injections for localizing the embolic occlusion and for positioning the catheter such that the energy delivery section 18 of the ultrasound catheter spans the thrombus. If the distal extent of the embolus is not visible angiographically or if it is difficult to probe the embolic occlusion, a 4 F Terumo® glide catheter may be used for obtaining very small selective contrast injections beyond the presumed thrombotic occlusion after transiently removing the 0.035 wire. After the wire is successfully placed beyond the thrombotic occlusion in a lower lobe segmental branch, the angiographic catheter is exchanged for the ultrasound catheter.

Finally, in embodiments wherein the ultrasound catheter including elongate inner core with ultrasound catheter (as shown in FIGS. 2-10) is used, the 0.035 guidewire can be removed and the elongate inner core with ultrasound radiating member(s) 40 is inserted into the ultrasound catheter. The therapeutic compound can be introduced through the at least one fluid delivery lumen 30 and out of the fluid delivery port(s) 58 to the treatment site. In embodiments wherein the ultrasound catheter exemplified in FIG. 11 is used, the therapeutic compound can be infused through the utility lumen 72 and out of the distal exit port 29 to the treatment cite. Infusion of the rt-PA at 1 mg/hr (20 ml/hr) and saline coolant at 10 ml/hr per catheter is then started and the ultrasound initiated.

After about 12 to about 15 hours of drug infusion, the rt-PA infusion can be replaced with heparinized saline infusion (about 1 µg/ml) at an infusion rate of 5 ml/hr. Sometime between about 16 and about 24 hours after the start of the rt-PA infusion, follow-up hemodynamic measurements (heart rate, systemic arterial pressure, right atrial, right ventricular and pulmonary artery pressures, mixed venous and pulse oximetric oxygen saturations, cardiac output, pulmonary vascular resistance) and controlled removal of the ultrasound catheter can be performed. The decision on the exact duration of the ultrasound-assisted thrombolysis infusion is at the discretion of the physician, but in one embodiment it is recommended to continue the treatment for 15 hours (or until 20 mg of rt-PA has been delivered) if well tolerated by the patient.

In certain embodiments, it can be beneficial to keep the catheter centered in the pulmonary artery during the treatment process. For example, centering the ultrasound radiating member 40 in the pulmonary artery may improve the uniform exposure at the treatment site. In some embodiments, the ultrasound catheter 10 also includes a centering mechanism for keeping the catheter centered during the treatment. For example, as shown in FIG. 15, the catheter 10 described herein can be provide with one or more balloons 102 disposed around the ultrasound catheter 10 toward the distal region 15. In some embodiments, the centering balloon 102 can be spirally wound around the catheter. When inflated, the spiral shaped balloon forms spiral lobes that keep the catheter centered in the pulmonary artery. In some embodiments, the centering balloon 102 can include or define flow paths such that the balloon 102 does not block blood flow.

In some embodiments, two or more balloons 102 are disposed radially around the ultrasound catheter 10. For example, in one arrangement one balloon can be positioned on a distal region of the catheter and another balloon can be positioned in a more proximal region of the catheter. These balloons can be inflated together or independently. Appropriate inflation lumens can be provided within the body of the catheter to provide inflation media to the balloon. In some embodiments, these balloons can also be expanded to different sizes, which allows the ultrasound catheter 10 to be positioned closer to certain areas of the treatment site while leaving larger distances between the catheter and other areas of the pulmonary artery wall. This allows certain areas of the treatment site to receive a larger dose of radiation and/or the drug. In addition, in some embodiments, the drug can be positioned between two balloons such that the concentration of the drug is kept in a desired treatment region. In yet another embodiment, the balloons can include a porous surface through which drug can be eluted through the balloon to a treatment site. In such arrangements, the balloon can be inflated with the drug. In other arrangements, the drug can be delivered to the porous surfaces of the balloon, while the balloon is inflated with a separate inflation media.

As described above, in some embodiments, the ultrasound assembly 42 comprises a plurality of ultrasound radiating members 40 that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control system 100. In some embodiments, two, three, or four or more than five groups of ultrasound radiating member 40 may be electrically connected to each other and the control system 100. Each group (G1-G5) may comprise one or more individual ultrasound elements. For example, in one embodiment, each group comprises five or less (i.e., one, two, three, four, or five) ultrasound radiating members 40. In other embodiments, more than 5 ultrasound elements can be provided in each group. Modified embodiments may also include different numbers of elements within each group.

In the embodiment of FIG. 6, each group G1-G5 comprises a plurality of ultrasound radiating members 40. Each of the ultrasound radiating members 40 is electrically connected to the common wire 108 and to the lead wire 110 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5.

The wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

Figure 16:
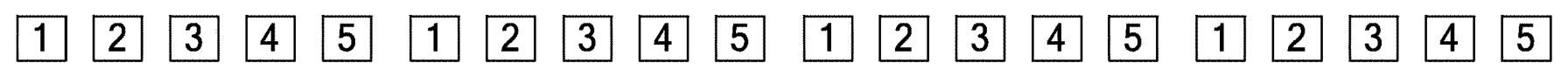

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group can be interdigitated with respect to ultrasound radiating members of a different group. FIG. 16 illustrates one example of such an arrangement. In this arrangement, elements of Group 1 (G1) are labeled "1", Group 2 (G2) are labeled "2" etc. In the illustrated arrangement, the elements of each group are interdigitated with members of another group in a 12345123451235123451237 pattern. As in the embodiments described above the elements within each group can be electrically connected to each other such that each group G1-5 can be individually powered (e.g., turned on or off and/or the amount of power or characteristic varied to each group). Accordingly, in this arrangement, when a single group is activated, ultrasonic energy can be delivered along a larger portion of the energy delivery section. In one embodiment, power to each group is controlled/modulated so as to keep temperature at the treatment site below a certain target temperature.

Figure 17A:
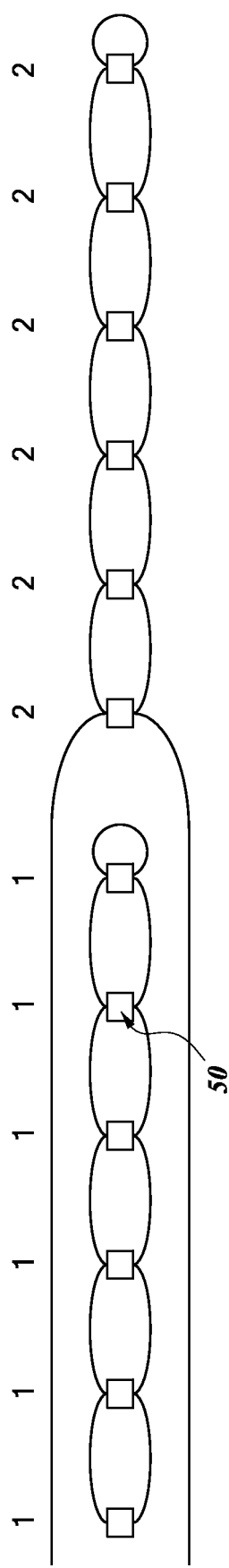
FIGS. 17A and 17B are schematic wiring diagrams illustrating techniques for electrically connecting groups of ultrasound radiating members to form an ultrasound assembly.
Figure 17B:
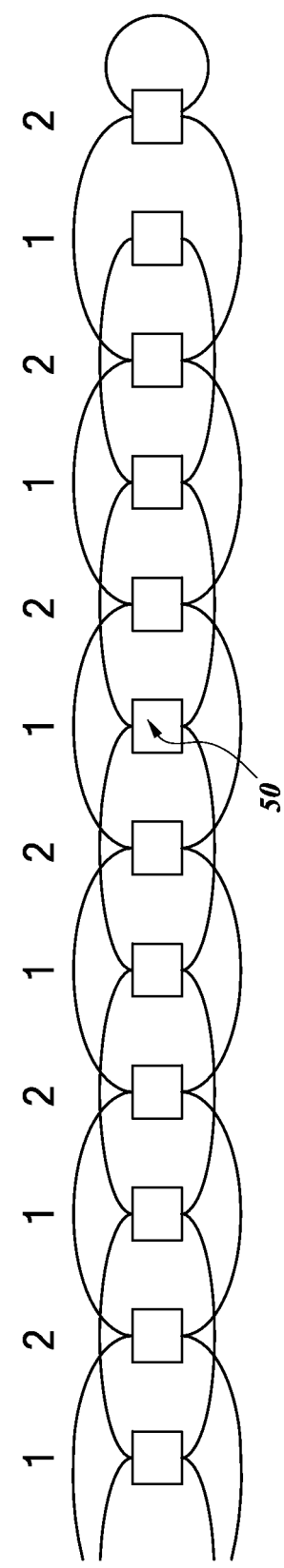

In modified arrangements, more or less groups or members per group can be used. In addition, the illustrated embodiment shows the elements interdigitated in a regular pattern. However, in modified arrangements the elements can be interdigitated in a random, pseudo random and/or a different pattern than that illustrated in FIG. 16. FIG. 17A schematically illustrates the arrangement of FIG. 5. The ultrasound radiating member pairs 50 of Group 1 (G1) are labeled "1", and the radiating member pairs 50 of Group 2 (G2) are labeled "2." In this embodiment, 6 ultrasound radiating member pairs 50 are wired together to form a group, and one group (e.g., G1) is positioned adjacent another group (e.g., G2). FIG. 17B illustrates two interdigitated groups similar to the example in FIG. 16. The radiating member pairs 50 of each group are interdigitated with the radiating member pairs 50 of another group, and the radiating member pairs 50 within each group are electrically connected to each other such that groups G1 and G2 can be individually powered.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein

What is claimed is:

1. A catheter system for delivering ultrasonic energy to a treatment site within a body lumen, the catheter comprising:
   a tubular body having a proximal end, a distal end and an energy delivery section positioned between the proximal end and the distal end; and
   a plurality of ultrasound radiating members positioned within the energy delivery section, the plurality of ultrasound radiating members being allocated into four or more electrical groups comprising three or more ultrasound radiating members, wherein each of the ultrasound radiating members of one electrical group is spatially interdigitated with each of the ultrasound radiating members of another electrical group, and wherein the three or more ultrasound radiating members of each electrical group are electrically connected together such that they can be powered together as a group and each electrical group is configured to be individually powered separately from the other electrical groups.

2. The catheter system of claim 1, wherein the plurality of ultrasound radiating members are mounted on an inner core, wherein the inner core is configured for insertion into the tubular body.

3. The catheter system of claim 1, further comprising at least one therapeutic compound delivery lumen that extends through the tubular body and terminates at least one outlet positioned in the energy delivery section.

4. The catheter system of claim 1, wherein the ultrasound radiating members are interdigitated in a regular pattern.

5. A catheter system for delivering ultrasonic energy to a treatment site within a body lumen, the catheter comprising:
- a tubular body having a proximal end, a distal end and an energy delivery section positioned between the proximal end and the distal end; and
- a plurality of ultrasound radiating members positioned within the energy delivery section, the plurality of ultrasound radiating members being allocated into at least three electrical groups comprising four or more ultrasound radiating members, wherein each of the ultrasound radiating members of one electrical group is spatially interdigitated with each of the ultrasound radiating members of another electrical group, and wherein the more than one ultrasound radiating members of each electrical group are electrically connected together such that they can be powered together as a group and each electrical group is configured to be individually powered separately from the other electrical groups.

6. The catheter system of claim 5, wherein the plurality of ultrasound radiating members are mounted on an inner core, wherein the inner core is configured for insertion into the tubular body.

7. The catheter system of claim 5, further comprising at least one therapeutic compound delivery lumen that extends through the tubular body and terminates at least one outlet positioned in the energy delivery section.

8. The catheter system of claim 5, wherein the ultrasound radiating members are interdigitated in a regular pattern.

* * * * *